(12) United States Patent
Szelinger et al.

(10) Patent No.: US 10,385,394 B2
(45) Date of Patent: Aug. 20, 2019

(54) PROCESSES OF IDENTIFYING AND CHARACTERIZING X-LINKED DISORDERS

(71) Applicant: THE TRANSLATIONAL GENOMICS RESEARCH INSTITUTE, Phoenix, AZ (US)

(72) Inventors: Szabolcs Szelinger, Phoenix, AZ (US); David W. Craig, Phoenix, AZ (US); Matthew Huentelman, Phoenix, AZ (US); Vinodh Narayanan, Phoenix, AZ (US)

(73) Assignee: The Translational Genomics Research Institute, Phoenix, AZ (US)

( * ) Notice: Subject to any disclaimer, the term of this patent is extended or adjusted under 35 U.S.C. 154(b) by 184 days.

(21) Appl. No.: 14/216,618

(22) Filed: Mar. 17, 2014

(65) Prior Publication Data
US 2014/0287934 A1  Sep. 25, 2014

Related U.S. Application Data

(60) Provisional application No. 61/794,245, filed on Mar. 15, 2013.

(51) Int. Cl.
*C12Q 1/6883* (2018.01)
*G16B 30/00* (2019.01)

(52) U.S. Cl.
CPC ........... *C12Q 1/6883* (2013.01); *G16B 30/00* (2019.02); *C12Q 2600/156* (2013.01)

(58) Field of Classification Search
None
See application file for complete search history.

(56) References Cited

U.S. PATENT DOCUMENTS 6,709,817 B1 * 3/2004 Zoghbi ................ C12Q 1/6883
435/6.13
9,127,312 B2 * 9/2015 Regan .................... C12Q 1/683

OTHER PUBLICATIONS

Robinson, et al. Integrative genomics viewer. Nature Biotechnology 2011; 29(1):24-26.
Dixon-Salazar, et al. Exome Sequencing Can Improve Diagnosis and Alter Patient Management. Science Translational Medicine 2012; 4(138):138ra78.
Yang, et al. Clinical Whole-Exome Sequencing for the Diagnosis of Mendelian Disorders. N Engl J Med 2013; 369 (16):1502-1511.
Gilissen, et al. Disease gene identification strategies for exome sequencing. Eur J Hum Gen 2012; 20:490-497.
Wang, et al. RNA-Seq: a revolutionary tool for transcriptomics. Nat Rev Genet 2009; 10:57-63.
Shah, et al. The clonal and mutational evolution spectrum of primary triple-negative breast cancers. Nature 2012, 486 (7403): 395-399.
Craig, et al. Genome and Transcriptome Sequencing in Prospective Metastatic Triple-Negative Breast Cancer Uncovers Therapeutic Vulnerabilities. Molecular Cancer Therapeutics 2013; 12(1):104-116.
Liang, et al. Genome-Wide Characterization of Pancreatic Adenocarcinoma Patients Using Next Generation Sequencing. PLoS ONE 2012; 7(10):e43192.
Babak, et al. Global Survey of Genomic Imprinting by Transcriptome Sequencing. Current Biology 2008; 18 (22):1735-1741.
Wang, et al. Transcriptome-Wide Identification of Novel Imprinted Genes in Neonatal Mouse Brain. PLoS ONE 2008; 3(12):e3839.
Lyon, M. F. Gene Action in the X-chromosome of the Mouse (Mus musculus L.). Nature 1961; 190:372-373.
Muller, H. J. Further studies on the nature and causes of gene mutations. Iln. Congr. Genet. 6 1932; 1:213-255.
Augui, et al. Regulation of X-chromosome inactivation by the X-inactivation centre. Nat Rev Genet 2011; 12(6):429-442.
Amos-Landgraf, et al. X Chromosome—Inactivation Patterns of 1,005 Phenotypically Unaffected Females. Am J Hum Genet 2006; 79:493-499.
Migeon, B. R. The Role of X Inactivation and Cellular Mosiacism in Women's Health and Sex-Specific Diseases. JAMA 2006; 295(12):1428-1433.
Ørstavik, K. H: X chromosome inactivation in clinical practice. Hum Genet 2009; 126:363-373.
Plenge, et al. Skewed X- chromosome inactivation is a common feature of X-linked mental retardation disorders. Am J Hum Genet 2002; 71:168-173.
Van Esch, et al. Duplication of the MECP2 region is a frequent cause of severe mental retardation and progressive neurological symptoms in males. Am J Hum Genet 2005; 77:442-453.
Allen, et al. Methylation of Hpall and Hhal sites near the polymorphic CAG repeat in the human androgen- receptor gene correlates with X chromosome inactivation. Am J Hum Genet 1992; 51:1229-1239.
Busque, et al. Skewing of X-inactivation ratios in blood cells of aging women is confirmed by independent methodologies. Blood 2009, 113(15):3472-3474.
Swierczek, et al. Methylation of AR locus does not always reflect X chromosome inactivation state. Blood 2012; 119:e100-e109.
Kim, et al. TopHat2: accurate alignment of transcriptomes in the presence of insertions, deletions and genefusions. Genome Biology 2013; 14:R36.
Rozowsky, et al. AlleleSeq: analysis of allele-specific expression and binding in a network framework. Molecular Systems Biology 2011; 7:522.
Stevenson, et al. Sources of bias in measures of allele-specific expression derived from RNA-seq data aligned to a single reference genome. BMC Genomics 2013; 14:536.
Li, et al. The Sequence Alignment/Map format and SAMtools. Bioinformatics 2009; 25(16):2078-2079.
Mangs, et al. The Human Pseudoautosomal Region (PAR): Origin, Function and Future. Current Genomics 2007; 8:129-136.

(Continued)

*Primary Examiner* — Joseph Woitach
(74) *Attorney, Agent, or Firm* — Rodney J. Fuller; Booth Udall Fuller, PLC

(57) ABSTRACT

The present invention relates to processes for characterizing and screening for the existence or predisposition to X-linked disorders associated with changes in X-chromosome inactivation. The present invention also relates to processes of reducing a disease phenotype associated with an X-linked disorder in a female subject.

19 Claims, 21 Drawing Sheets

Specification includes a Sequence Listing.

(56) References Cited

OTHER PUBLICATIONS

McKenna, et al. The Genome Analysis Toolkit: A MapReduce framework for analyzing next-generation DNA sequencing data. Genome Research 2010; 20(9):1297-1303.
Skelly, et al. A powerful and flexible statistical framework for testing hypotheses of allele-specific gene expression from RNA-seq data. Genome Research 2011; 21:1728-1737.
Zho et al. A powerful and flexible approach to the analysis of RNA sequence count data. Bioinformatics 2011; 27 (19):2672-2678.
Hardcastle, et al. Empirical Bayesian analysis of paired high-throughput sequencing data with a beta-binomial distribution. BMC Bioinformatics 2013; 14:135.
Sun, W. A Statistical Framework for eQTL Mapping Using RNA-seq Data. Biometrics 2012; 68(1):1-11.
Hunter, et al. Inference for mixtures of symmetric distributions. Ann Statist 2007; 35(1):224-251.
Bordes, et al. A stochastic EM algorithm for a semiparametric mixture model. Computational Statistics & Data Analysis 2007; 51:5429-5443.
Li, et al. Fast and accurate short read alignment with Burrows-Wheeler transform. Bioinformatics 2009; 25(14):1754-1760.
Depristo, et al. A framework for variation discovery and genotyping using next-generation DNA sequencing data. Nature Genetics 2011; 43(5):491-498.
Trapnell, et al. Transcript assembly and quantification by RNA-Seq reveals unannotated transcripts and isoform switching during cell differentiation. Nature Biotechnology 2010; 28(5):511-515.
Carrel, et al. X-inactivation profile reveals extensive variability in X-linked gene expression in females. Nature 2005; 434(7031):400-404.
Zhang, et al. Genes That Escape X-Inactivation in Humans Have High Intraspecific Variability in Expression, Are Associated with Mental Impairment but Are Not Slow Evolving. Mol. Biol. Evol. 2013; 30(12):2588-2601.
Morgan, et al. The propeptide precursor proSAAS is involved in fetal neuropeptide processing and body weight regulation. Journal of Neurochemistry 2010; 113:1275-1284.
Disteche, C. M. Escapees on the X chromosome. Proc Natl Acad Sci USA 1999; 96(25):14180-14182.
Jiao, et al. Modulation of Neuritogenesis by a Protein Implicated in X-Linked Mental Retardation. Journal of Neuroscience 2009; 29(40):12419-12427.
Van Esch, et al. Deletion of VCX-A due to NAHR plays a major role in the occurrence of mental retardation in patients with X-linked ichthyosis. Human Molecular Genetics 2005; 14(13):1795-1803.
Liu, et al. Copy number gain at Xp22.31 includes complex duplication rearrangements and recurrent triplications. Human Molecular Genetics 2011; 20(10):1975-1988.
Desai, et al. Favorably skewed X-inactivation accounts for neurological sparing in female carriers of Menkes disease. Clinical Genetics 2011; 79:176-182.
Li, et al. Interstitial microduplication of Xp22.31: Causative of intellectual disability or benign copy number variant? European Journal of Medical Genetics 2010; 53:93-99.
Bittel, et al. Comparison of X-chromosome inactivation patterns in multiple tissues from human females. Journal of Medical Genetics 2008; 45:309-313.
Scherzer, et al. Molecular markers of early Parkinson's disease based on gene expression in blood. Proc Natl Acad Sci USA 2007; 104(3):955-960.
Borovecki, et al. Genome-wide expression profiling of human blood reveals biomarkers for Huntington's disease. Proc Natl Acad Sci USA 2005; 102(31):11023-11028.
Biliya, et al. Genomic imprinting: the influence of differential methylation in the two sexes. Experimental Biology and Medicine 2010; 235:139-147.
Moreira, et al. Random X Inactivation and Extensive Mosaicism in Human Placenta Revealed by Analysis of Allele-Specific Gene Expression along the X Chromosome. PLoS ONE 2010; 5(6):e10947.
Swierczek, et al. Hematopoiesis is not clonal in healthy elderly women. Blood 2008; 112:3186-3193.

\* cited by examiner

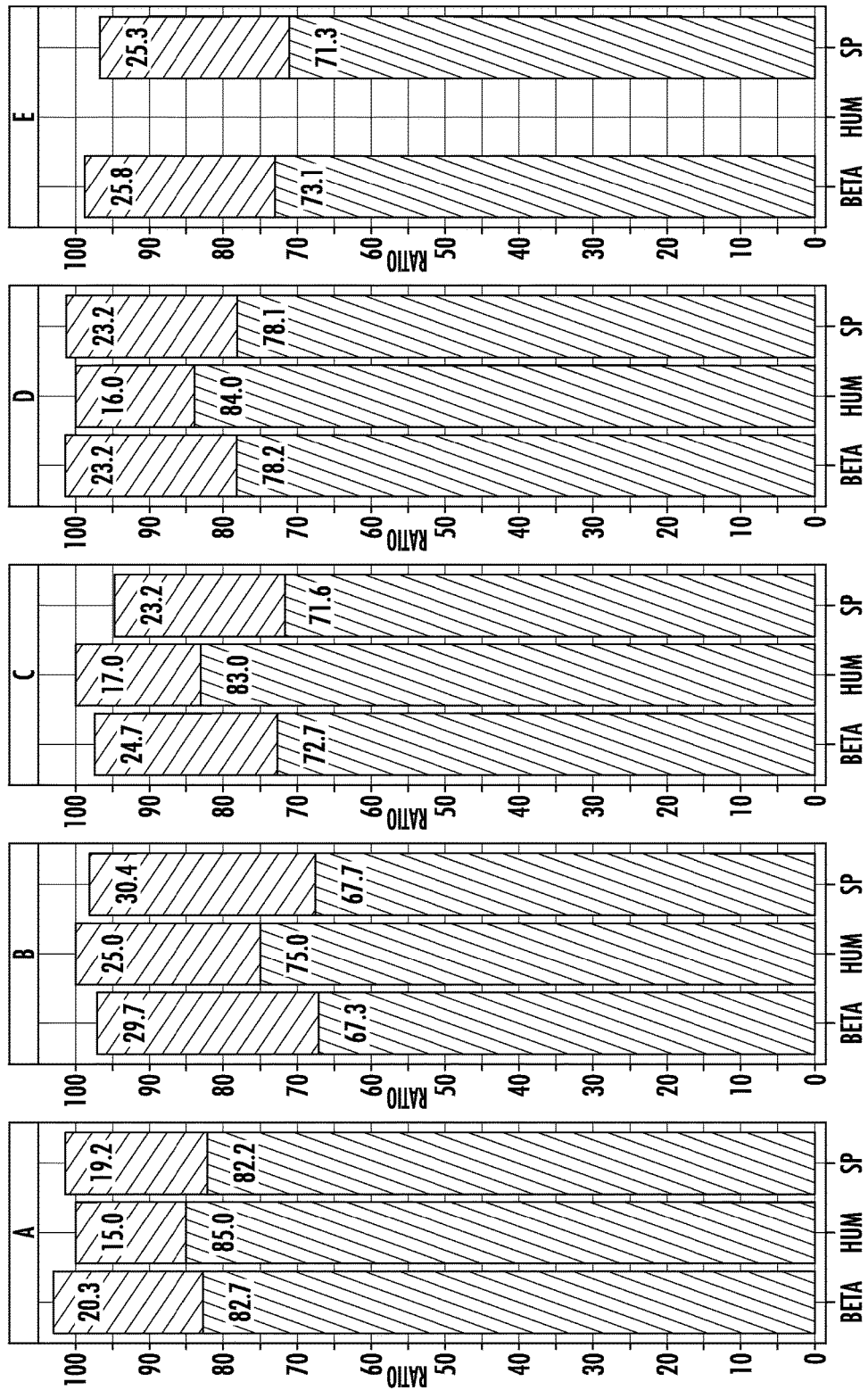

PROCESSES OF IDENTIFYING AND CHARACTERIZING X-LINKED DISORDERS

CROSS-REFERENCE TO RELATED APPLICATIONS

The present application claims priority to U.S. Application No. 61/794,245, filed Mar. 15, 2013, the entire contents and disclosure of which are herein incorporated by reference thereto.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 763 kilobyte ASCII (text) file named "91482_125_Sequence_Listing_ST25" created on Jun. 11, 2014.

TECHNICAL FIELD

The present invention relates to an integrated high throughput sequencing process to characterize X chromosome inactivation (XCI) in a female subject and to processes of identifying and characterizing X-linked disorders associated with X chromosome inactivation ratios. The present invention also relates to a method of reducing a disease phenotype associated with an X-linked disorder.

BACKGROUND

Diagnosing and uncovering the genetic basis of disease has been revolutionized by whole-exome sequencing (WES), allowing discovery of new disease genes and improving the rate of clinical diagnosis for rare genetic conditions. Indeed, the genetic basis of childhood disorders can be identified in approximately 25% of clinical cases, where successful molecular diagnosis frequently has a major impact on patient management and treatment[1, 2]. Prioritization of candidate variants in the remaining cases remains challenging due mainly to insufficient understanding of the functional consequence of substantial fraction of candidate variants[3]. Large scale functional characterization of genomic variation by simultaneously sequencing RNA from the patient can reveal genotype-phenotype correlation, can highlight gene expression profile that is associated with the studied genetic condition, and allows immediate evaluation of in silico prediction algorithms to the effect genomic variants have on gene expression, alternative splicing, exon usage, gene fusions[4]. In breast and pancreatic cancer integrated analysis of DNA and RNA has been successfully utilized to obtain insight into molecular mechanisms that explain pathogenicity and uncovered potential therapeutic targets to improve patient management[5-7]. In addition, sequencing RNA (RNAseq) has been utilized in the context of the effect epigenetic modifications have on gene expression [8, 9]. Integrative analysis of whole-exome and RNA sequencing data in X-linked disorders may also be informative both in diagnosis and gene discovery for phenotypes emerging due to epigenetic changes such as X chromosome inactivation[10].

In the process of X-chromosome inactivation (XCI), in females, cells undergo epigenetic inactivation of one of the inherited, parental X chromosomes resulting in consecutive daughter cells expressing one X [11, 12]. The proportion of cells with either parental X as the active is defined by the XCI ratio that ranges from 50:50 random to 100:0 completely skewed. Epigenetic analysis of X chromosome in unaffected females indicate that XCI ratio varies in the general population and is normally distributed [13]. Although, on the cellular level X-linked alleles are expressed in a dominant fashion due to XCI, in cell populations they show mosaic pattern which can lead to heterogeneous phenotype in females who are carriers for disease causing, deleterious mutations[14].

In X-linked neurological disease, mode and magnitude of XCI can influence disease severity and outcome [15]. Indeed, case-control studies demonstrate that skewed XCI is common among females who are carriers for X-linked Mental Retardation disorders (XMLR)[16]. XCI may also lead to asymptomatic carrier status by selective advantage of cells expressing the wild-type alleles[17]. One of the difficulties diagnosing females with X-linked diseases and skewed XCI is the broad and overlapping description of clinical phenotype, the limited availability of similar cases, and lack of high-throughput expression-based methods to estimate XCI[15]. Routine, clinical method to estimate XCI ratio rely on the HUMARA differential DNA methylation assay that targets a polymorphic short tandem repeat (STR) in the human androgen receptor gene (AR)[18]. Methylation of this repeat is associated with X chromosome inactivation. Although >90% females are polymorphic at this site to differentiate between the two chromosome copies, it provides expression information indirectly from DNA, and, relies on a single locus[13]. There is also conflicting evidence whether DNA methylation can reflect the quantitative expression ratio of active and inactive X with high accuracy when compared to direct allelic expression-based methods [19, 20].

Thus, a need exist for an improved processes for scanning for and analyzing these X-linked variations and simultaneously obtaining functional implications of those genomic variations.

SUMMARY

The present invention relates generally to processes and kits for identifying and characterizing an X-linked disorder associated with changes in X-chromosome inactivation. The present invention also relates to therapies for preventing and/or reducing the severity of the X-linked disorder in the subject.

In one aspect, the present invention provides an integrated high throughput sequencing process to identify and characterize X-linked disorders and X-chromosome inactivation abnormalities. The process generally comprises obtaining a biological sample from the subject and isolating nucleic acids from the biological sample. The process also comprises performing whole genome sequencing or whole exome sequencing by next generation sequencing of the isolated nucleic acids; performing whole transcriptome sequencing by next generation sequencing of the isolated nucleic acids; and identifying at least one X-linked variant allele associated with a phenotype of the X-linked disorder.

In certain embodiment, the whole transcriptome sequencing comprises whole mRNA sequencing and is performed simultaneously with the whole genome sequencing or whole exome sequencing. The process also preferably is performed on a family trio, wherein the family trio comprises of the subject with the X-linked disorder, the biological mother of the subject and the biological father of the subject. In yet another aspect, the integrated sequencing process provides information on chromosome-wide X-linked heterozygous SNP alleles. The X-linked disorder is often, at least partially, caused by a change in mode and magnitude of XCI.

In a particular embodiment, the process also includes determination of the mode of XCI. Mode is defined as the parental origin of unbalanced X inactivation ratio. The mode of XCI can be determined by phasing the transmission of X chromosome-wide heterozygous SNP alleles of the subject. In another embodiment, the magnitude of XCI ratio is determined by allele-specific expression analysis of phased or unphased chromosome-wide X-linked heterozygous SNP alleles of the subject that are transcribed into mRNA. In yet other embodiment, the XCI ratio was estimated from phased heterozygous SNPs by beta parametric model and the XCI ratio was estimated from unphased heterozygous SNPs by semi-parametric model and the XCI ratio can be estimated from unphased heterozygous SNPs by semi-parametric model. In another embodiment, a combination of the change in mode and magnitude of XCI and the presence of the at least one genomic or functional biomarker is responsible for the phenotype for the X-linked disorder.

In a certain nonlimiting embodiment, the magnitude of XCI can be determined in silico by computer simulation of phased or unphased chromosome-wide X-linked heterozygous SNP alleles of the subject or the magnitude of XCI is determined by allele-specific expression analysis of phased or unphased chromosome-wide X-linked heterozygous SNP alleles of the subject that are transcribed into mRNA.

In an exemplary aspect, the X-linked disorder is a neurobehavioral condition manifesting at least an emotional instability, attention deficit, or delays in development and learning. In certain embodiment, the biological sample comprises a blood sample or a brain tissue sample from the subject. In a particular embodiment, the at least one X-linked variant allele comprises a large chromosomal deletion and/or amplification. In another embodiment, the large chromosomal deletion and/or amplification is detected by plotting log 2 differences, $$\log2\left(\frac{\text{\# reads mapping to 100 bp window affected}}{\text{\# reads mapping to all windows in affected}}\right) - \log2\left(\frac{\text{\# reads mapping to 100 bp window } mom}{\text{\# reads mapping to all windows in } mom}\right)$$

of approximately −1, means a heterozygous deletion in one of the chromosome copies in the regions of interest. A score of −2 would indicate a homozygous loss of both chromosome copies at the location of interest, a +1 would indicate a copy gain (amplification) and a +2 would indicate a homozygous copy gain. In certain aspects, the at least one X-linked variant allele comprise an interstitial deletion in a region of the X-chromosome. For example, the interstitial deletion can be in the region of the X-chromosome harbors at least five genes comprising VCX3A, HDHD1, STS, VCX, PNPLA4 and two microRNA genes comprising miR-4767, miR-651. In one non-limiting specific example, the deletion is a heterozygous 1.7 Mb deletion on the Xp22.31 locus of the X-chromosome between 6,451,600 bp and 8,095,100 bp.

In yet another aspect, the deletion is characterized as a de novo mutation by co-segregation analysis of parental genotypes obtained from whole exome sequencing. In certain aspects, the source of the de novo interstitial deletion is paternal X-chromosome as identified by phasing of X-chromosome wide heterozygous SNP alleles. The phasing of the deletion provides mode or direction of XCI as paternal X-chromosome in certain embodiment. The magnitude of XCI or XCI ratio is preferably estimated in silico by computer simulation of phased or unphased chromosome wide X-linked heterozygous SNP alleles, or the XCI ratio is estimated by allele-specific mRNA expression analysis of phased or unphased chromosome wide X-linked heterozygous SNP alleles that are transcribed into mRNA. In certainly embodiments, the combination of mode and magnitude of skewedness in XCI and the interstitial deletion of at least one gene is identified as being responsible for the phenotype for the X-linked disorder.

In a second aspect of the invention, the invention comprises a therapy for preventing or reducing a disease phenotype associated with an X-linked disorder in a female subject.

In certain aspects, the therapy further comprises identifying in the subject a skewed (i.e., non-random XCI) and treating the subject for correction of effects of the skewed or non-random XCI. In a particular embodiment of the treatment, the at least one X-linked variant allele associated with the X-linked disorder is a variation in at least one gene selected from the group consisting of VCX3A, HDHD1, STS, VCX, PNPLA4, miR-4767, miR-651.

In a third aspect of the invention, the invention comprises a process of determining skewedness in monoallelic expression of autosomal or X-chromosomal genes in a biological sample, the process comprising subjecting the sample to integrated whole genome sequencing or exome sequencing and whole transcriptome sequencing, and calculating allelic skewedness ratio by allelic specific distribution analysis of phased or unphased chromosome-wide heterozygous SNP alleles that transcribed into mRNA, or simulating RNA sequencing reads in silico with chromosome-wide heterozygous SNP alleles and calculating allelic skewedness ratio by analysis of phased or unphased chromosome-wide heterozygous SNP variants from the simulated data.

In one embodiment, the simulation of RNA sequencing reads in silico is by a process that comprises introducing nucleotide changes into a reference chromosome of interest from the ESP6500 NHLBI Exome Sequencing Project by selecting a number of chromosome wide SNPs from a database of subjects; separating randomly the SNPs into two groups, one group analogous to variant alleles on maternal chromosome referred to as pseudo-maternal variant SNPs and the other group analogous to variant alleles on paternal chromosome referred to as pseudo-paternal variant SNPs; introducing the pseudo-maternal and pseudo-paternal variant SNPs into two separate chromosome X fasta files and reducing the two fasta files to greater than 500 bp regions that correspond to known transcripts according to human genome annotation *Homo sapiens* GRCh37.62.gtf file so as to obtain two separate transcriptome files; generating 10 million, 100 bp paired reads mapping to the two separate transcriptome files using wgsim 0.3.1-r13 fastq simulator; and sub sampling the 10 million paired reads randomly in various ratios and merging the randomly distributed reads into a single fastq file. In other embodiment, the skewedness in monoallelic expression of genes serves as a marker for identification of autosomal disorders or X-linked disorders.

In a fourth aspect of the invention, the invention comprises of a kit for screening for the existence of an X-linked disorder and/or a predisposition for a X-linked disorder in a subject. The kit typically comprises at least one genomic or functional biomarker selected from the group consisting of VCX3A, HDHD1, STS, VCX, PNPLA4, miR-4767, and miR-651, and/or at least one biomarker for detecting skewedness or non-randomness of XCI to specifically determine the expression severity of the X-linked disorder and/or a predisposition to the X-linked disorder.

BRIEF DESCRIPTION OF THE DRAWINGS

FIG. 6A shows a chromosomal view of log 2 coverage difference between affected child and mother obtained by exome sequencing. The log 2 difference of normalized read coverage between affected child and mother is shown on the y axis, with each blue dot indicating log 2 difference in normalized sequence coverage in a 100 bp window. The red line across the chromosome is the mean log 2 differences across a sliding window of 25. A large deletion on chromosome X is recognizable in the child indicated by drop in log 2 difference to −1 between 0-10Mbase. FIG. 6B shows a zoomed in view of reduced sequence read coverage between 6.4-8.1Mbase of the short arm of the chromosome. The pink shaded area indicates the deletion breakpoints predicted by CGH analysis that overlaps with deletion seen by the exome coverage analysis. Gene tracks above the x axis were obtained from UCSC Genome Browser and contain the deleted genes VCX3A, HDHD1, STS, VCX, PNPLA4 genes and M14767 microRNA genes.

FIGS. 9A-9E show estimation of XCI pattern using 3 different processes. Stacked columns show the estimated XCI ratios for 5 females with RNAseq and HUMAR assay performed. XCI ratios were determined from RNAseq by beta testing of the allelic distribution of phased, X-linked alleles (Beta), Semi-Parametric fit of unphased X-linked alleles (SP), and HUMARA assay (Hum). FIG. 9A indicates the clinical case in this study and FIGS. 9B, 9C, 9D, 9E indicate additional females from our clinical sequencing center. For the Beta and SP columns, the red bar indicates the mean allelic ratio of the first component of chromosome-wide allelic distribution, and the turquoise bar indicates the mean allelic ratio of the second component of the distribution. In the Hum column the red bar indicates the percentage of cells with allele 1 of the AR locus, and the blue bar indicates the percentage of cells with allele2 of the AR locus.

FIG. 9E was uninformative for the HUMARA assay due to homozygosity at the AR locus.

DETAILED DESCRIPTION

Figure 1:
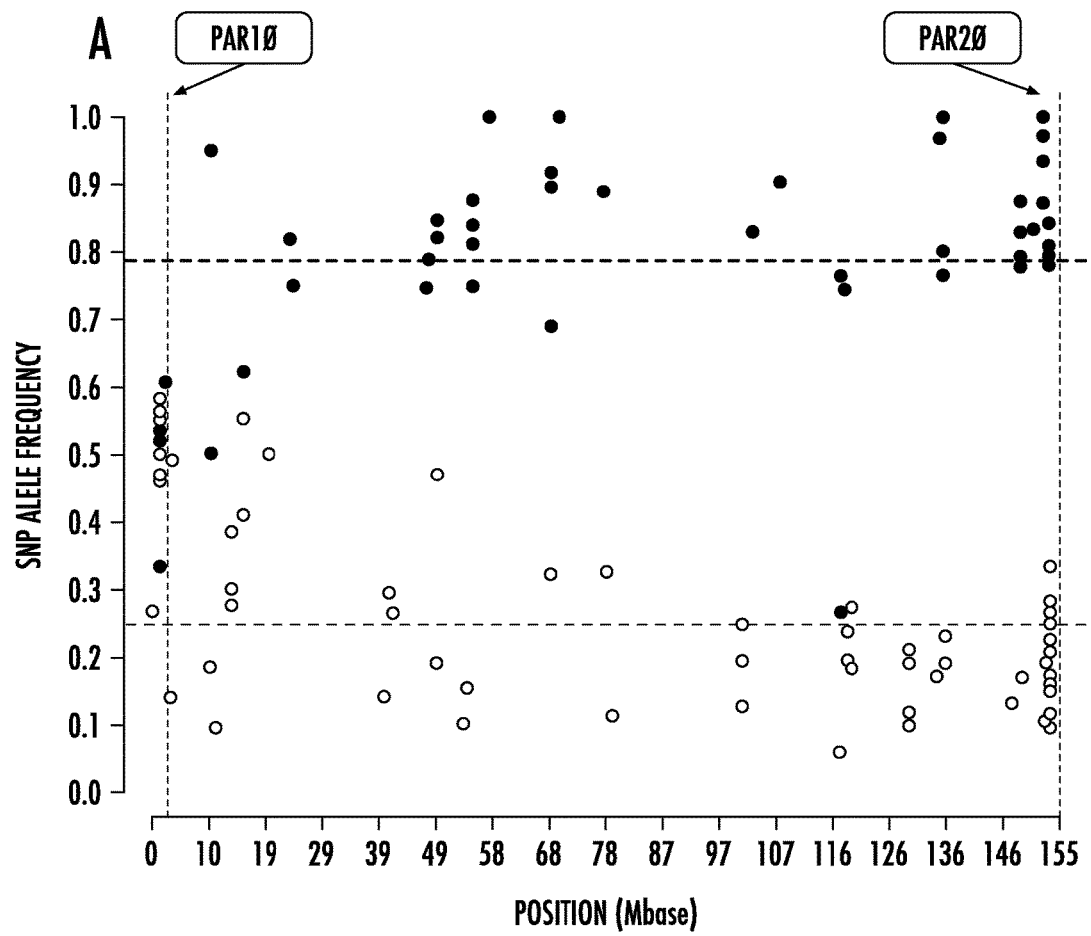
FIG. 1 shows expression of parent-of-origin SNP alleles across X Chromosome. Plots demonstrate skewed expression of SNP alleles towards the maternally inherited SNPs in the pro band (A) when compared to an unrelated female-individual with no skewed X inactivation (B) Based on analysis of two families trio whole exome SNP sets, high quality heterozygous SNPs were selected for the affected pro band (A) and an unrelated female individual (B). Heterozygous SNP loci were phased for parent-of-origin. For each phased genomic loci, the number of reads were counted mapping to reference—and alternative alleles in the pileup of the transcriptome sequencing variants set. Next,—SNP frequency was calculated quantifying any deviation from the 0.5 expected frequency if maternal and paternal chromosomes are inactivated randomly. Pro band (A) shows that maternally inherited SNPs have a higher frequency of expression (red dots) when compared to the frequency of paternally inherited SNPs (green dots) indicating that X-inactivation is a non-random process. Vertical lines indicate Pseudo autosomal Region1 (PAR1) and Pseudo autosomal Region 2 (PAR2). Horizontal lines are the mean frequencies of maternally inherited SNPs (red dots) and paternally inherited SNPs (green dots). Red and green triangles (A) indicate allele frequency for maternally and paternally inherited SNPs in genes that are associated with escape from X inactivation per our—literature search.
Figure 1:
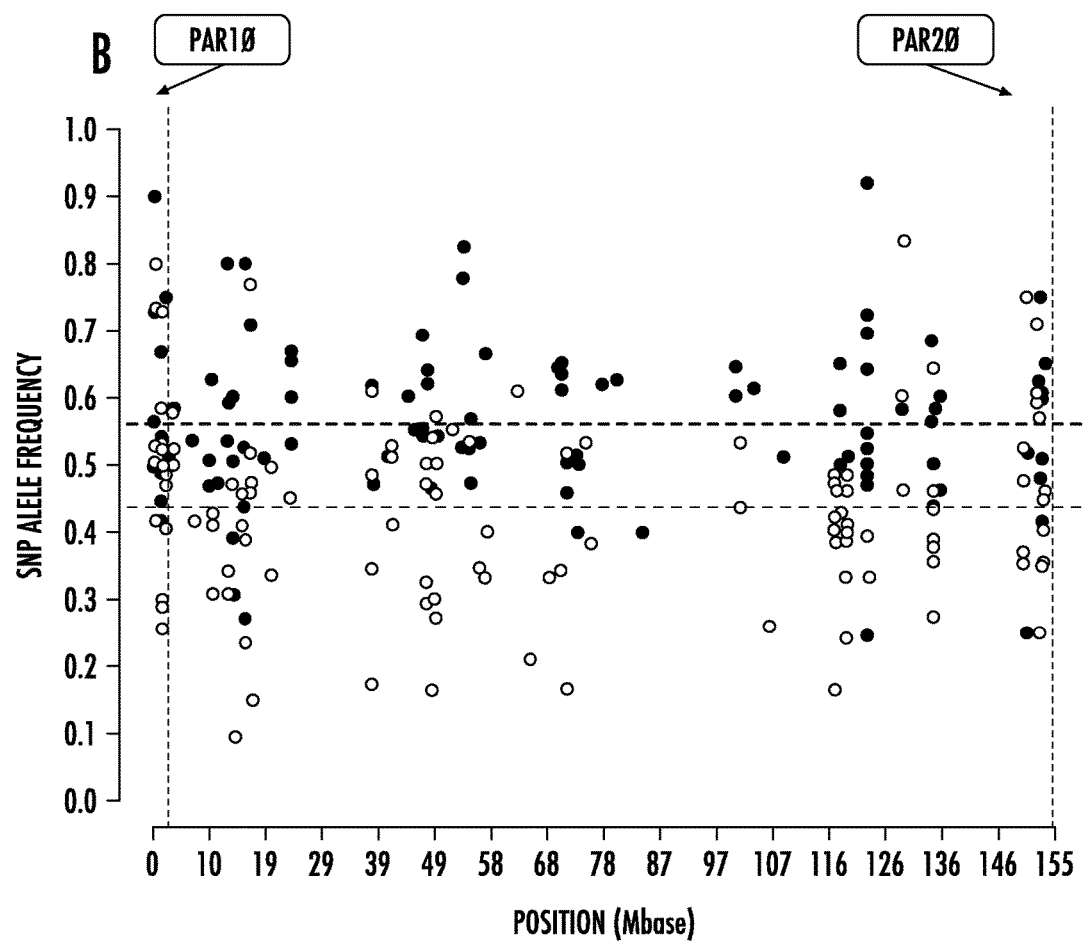

As used herein, the verbs "comprise" and "include" as used in this description and in the claims and their conjugations are used in their non-limiting sense to mean that items following the words are included, but items not specifically mentioned are not excluded. For example, a process, method, system, composition, kit, or apparatus that comprises a list of features is not necessarily limited only to those features but may include other features not expressly listed or inherent to such process, method, system, composition, kit, or apparatus. In addition, reference to an element by the indefinite article "a" or "an" does not exclude the possibility that more than one of the elements are present, unless the context clearly requires that there is one and only one of the elements. The indefinite article "a" or "an" thus usually means "at least one".

As used herein, the term "subject" or "patient" refers to any vertebrate including, without limitation, humans and other primates (e.g., chimpanzees and other apes and monkey species), farm animals (e.g., cattle, sheep, pigs, goats and horses), domestic mammals (e.g., dogs and cats), and laboratory animals (e.g., rodents such as mice, rats, and guinea pigs). In preferred implementations, the subject may be a human.

As used herein, the term "biological sample" is used in its broadest sense and can refer to a bodily sample obtained from a subject (e.g., a human). For example, the biological sample can include a "clinical sample", i.e., a sample derived from a subject. Such samples can include, but are not limited to: peripheral bodily fluids, which may or may not contain cells, e.g., blood, urine, plasma, mucous, bile pancreatic juice, supernatant fluid, and serum; tissue or fine needle biopsy samples; and archival samples with known diagnosis, treatment and/or outcome history. Biological samples may also include sections of tissues, such as frozen sections taken for histological purposes. The term "biological sample" can also encompass any material derived by processing the sample. Derived materials can include, but are not limited to, cells (or their progeny) isolated from the biological sample and proteins extracted from the sample. Processing of the biological sample may involve one or more of, filtration, distillation, extraction, concentration, fixation, inactivation of interfering components, addition of reagents, and the like.

As used herein, the term "nucleic acid" refers to a polymeric form of nucleotides of any length, either ribonucleotides or deoxyribonucleotides, or analogs thereof. This term refers to the primary structure of the molecule, and thus includes double- and single-stranded DNA, as well as double- and single-stranded RNA. It also includes modified nucleic acids such as methylated and/or capped nucleic acids, nucleic acids containing modified bases, backbone modifications, and the like. The terms "nucleic acid" and "nucleotide sequence" are used interchangeably.

As used herein, the term "gene" refers to a nucleic acid or portion of a nucleic acid comprising a sequence that encodes a protein. It is understood in the art that a gene also comprises non-coding sequences, such as 5' and 3' flanking sequences (such as promoters, enhancers, repressors, and other regulatory sequences) as well as introns.

As used herein, the terms "polynucleotide", "polynucleotide sequence", "nucleic acid sequence", "nucleic acid fragment", and "isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

As used herein, the terms "polypeptide," "peptide," and "protein" are used interchangeably herein to refer to polymers of amino acids of any length. These terms also include proteins that are post-translationally modified through reactions that include glycosylation, acetylation and phosphorylation.

As used herein, the term "nucleotide change" refers to, e.g., nucleotide substitution, deletion, and/or insertion, as is well understood in the art. For example, mutations can be those containing alterations that produce silent substitutions, additions, or deletions, but do not alter the properties or activities of the encoded protein or how the proteins are made.

As used herein, the term "protein modification" refers to, e.g., amino acid substitution, amino acid modification, deletion, and/or insertion, as is well understood in the art.

As used herein, "coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence.

As used herein, the "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht, I. L., et al. (1989) Plant Cell 1:671-680.

As used herein, the term "predisposition" or "predisposed" when used with respect to X-linked disorder refers to an individual who is more susceptible to develop X-linked disorder than non-predisposed individuals. It should be noted that the predisposition is determined when the subject is free of the X-linked disorder or not yet diagnosed with the X-linked disorder.

As used herein, the term "wild-type gene" refers to an allele that is most commonly found in nature or is otherwise designated normal. For the purpose of the present invention, the term "wild-type gene" means a normal gene.

As used herein, the term "mutant gene" refers to a gene that differs from a wild-type gene in DNA structure and sequence or function.

As used herein, the term "mutation" is meant to include all kinds of nuclear and/or mitochondrial gene mutations, including point mutations and small insertion/deletion mutations (e.g., 1-50-bp insertion or deletion mutation). Mutations can lead to changes in the structure of an encoded protein or to a decrease or complete loss in its expression. Because a change in the DNA sequence affects all copies of the encoded protein, mutations can be particularly damaging to a cell or organism. In contrast, any alterations in the sequences of RNA or protein molecules that occur during their synthesis are less serious because many copies of each RNA and protein are synthesized.

The term "deletion mutation," as used herein, refers to the removal or loss of one or more nucleotides from a nucleic acid sequence, and is also referred to in the art as a "gene deletion," a "deficiency," or a "deletion." The term "insertion mutation" (or "insertion"), as used herein, refers to the addition of one or more nucleotides into a nucleic acid sequence. The term "chromosome amplification" or "gene amplification" or "amplification" as used herein, refers to an increase in the number of copies of a gene or a number of genes in an organism's genome.

As used herein, the term "sequencing" and its variants comprise obtaining sequence information from a nucleic acid strand, typically by determining the identity of at least some nucleotides (including their nucleobase components) within the nucleic acid molecule. The term sequencing may also refer to determining the order of nucleotides (base sequences) in a nucleic acid sample, e.g. DNA or RNA. Many techniques are available such as Sanger sequencing and high-throughput sequencing technologies (also known as next-generation sequencing technologies) such as the GS FLX platform offered by Roche Applied Science, based on pyro sequencing.

As used herein, the phrase "next generation sequencing" refers to sequencing technologies having increased throughput as compared to traditional Sanger- and capillary electrophoresis-based approaches, for example with the ability to generate hundreds of thousands or millions of relatively small sequence reads at a time. Some examples of next generation sequencing techniques include, but are not limited to, sequencing by synthesis, sequencing by ligation, and sequencing by hybridization. Examples of next generations sequencing processes include pyrosequencing as used by 454 Corporation, Illumina's Solexa system, the SOLiD™ (Sequencing by Oligonucleotide Ligation and Detection) system (Life Technologies Inc.), and Ion Torrent Sequencing systems such as the Personal Genome Machine or the Proton Sequencer (Life Technologies Inc.)

As used herein, the term "alignment" refers to positioning of multiple sequences in a tabular presentation to maximize the possibility for obtaining regions of sequence identity across the various sequences in the alignment, e.g. by introducing gaps. Several methods for alignment of nucleotide sequences are known in the art, as will be further explained below.

The term "heterozygous" refers to a condition in which different alleles exist at corresponding loci on homologous chromosomes, while the term "homozygous" refers to a condition in which identical alleles exist at corresponding loci on homologous chromosomes.

As used herein, "treatment" and "treating" and the like generally mean obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it such as a preventive early asymptomatic intervention; (b) inhibiting the disease, i.e., arresting its development; or relieving the disease, i.e., causing regression of the disease and/or its symptoms or conditions such as improvement or remediation of damage.

As used herein, an "allele" refers to an alternative sequence at a particular locus. In this invention, "allele" includes all variants and differences in a gene, including deletions, amplifications, or a difference as small as one nucleotide base.

As used herein, a "locus" is a short sequence that is usually unique and usually found at one particular location in the genome by a point of reference, e.g., a short DNA sequence that is a gene, or part of a gene or intergenic region. In some embodiments, a locus is a unique PCR product at a particular location in the genome. Loci may comprise one or more polymorphisms; i.e., alternative alleles present in some individuals.

As used herein, the term "variant" when used in reference to a nucleotide sequence refers to a nucleic acid sequence that differs by one or more nucleotides from another, including deletions and amplifications.

As used herein, "polymorphism" means the presence of one or more variations of a nucleic acid sequence at one or more loci in a population of one or more individuals. The variation may comprise but is not limited to one or more base changes, the insertion of one or more nucleotides or the deletion of one or more nucleotides. A polymorphism includes a single nucleotide polymorphism (SNP), a simple sequence repeat (SSR) and indels, which are insertions and deletions. A polymorphism may arise from random processes in nucleic acid replication, through mutagenesis, as a result of mobile genomic elements, from copy number variation and during the process of meiosis, such as unequal crossing over, genome duplication and chromosome breaks and fusions. The variation can be commonly found or may exist at low frequency within a population, the former having greater utility in general plant breeding and the later may be associated with rare but important phenotypic variation. In some embodiments, a "polymorphism" is a variation among individuals in sequence, particularly in DNA sequence, or feature, such as a transcriptional profile or methylation pattern. Useful polymorphisms include single nucleotide polymorphisms (SNPs), insertions or deletions in DNA sequence (indels), simple sequence repeats of DNA sequence (SSRs) a restriction fragment length polymorphism, a haplotype, and a tag SNP. A genetic marker, a gene, a DNA-derived sequence, a RNA-derived sequence, a promoter, a 5' untranslated region of a gene, a 3' untranslated region of a gene, microRNA, siRNA, a QTL, a satellite marker, a transgene, mRNA, ds mRNA, a transcriptional profile, and a methylation pattern may comprise polymorphisms.

As used herein, "genotype" refers to the entire set of genes carried by an individual, whereas "phenotype" refers to the function and physical appearance of an individual. Phenotype also refers more broadly to characteristics, properties, attributes, functions, etc., that may result from a combination of two or more phenotypic characteristics.

As used herein, the term "exome" refers to the collection of genomic segments that include protein coding regions, exons, promoters, known ncRNAs (non-coding RNAs) and UTRs, altogether comprising about 2% of the human genome.

As used herein, the term "transcriptome" means a collection of RNA transcripts transcribed in a specific tissue, whether coding or non-coding, and preferably contains all or substantially all of the RNA transcripts generated in the tissue. These transcripts include messenger RNAs (mRNA), alternatively spliced mRNAs, ribosomal RNA (rRNA), transfer RNAs (tRNAs) in addition to a large range of other transcripts, which are not translated into protein such as small nuclear RNAs (snRNAs), antisense molecules such as short interfering RNA (siRNA) and .microRNA and other RNA transcripts of unknown function. Thetranscriptome also includes proteins translated from the RNA transcripts within the transcriptome, which is an extension and reflection of gene transcription within the transcriptome.

As used herein, the term "isolated" when used in relation to a nucleic acid, as in "an isolated nucleic acid" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids, such as DNA and RNA, are found in the state they exist in nature. Examples of non-isolated nucleic acids include: a given DNA sequence (e.g., a gene) found on the host cell chromosome in proximity to neighboring genes, RNA sequences, such as a specific mRNA sequence encoding a specific protein, found in the cell as a mixture with numerous other mRNAs which encode a multitude of proteins. However, isolated nucleic acid encoding a particular protein includes, by way of example, such nucleic acid in cells ordinarily expressing the protein, where the nucleic acid is in a chromosomal location different from that of natural cells, or is otherwise flanked by a different nucleic acid sequence than that found in nature. The isolated nucleic acid or oligonucleotide may be present in single-stranded or double-stranded form.

As used herein, the term "neurological disorder" or "neurodegenerative disorder" or "neurological dysfunction" refers to an impairment or absence of a normal neurological function or presence of an abnormal neurological function in a subject. For example, neurological disorders can be the result of disease, injury, and/or aging. As used herein, neurological disorder also includes neuro degeneration which causes morphological and/or functional abnormality of a neural cell or a population of neural cells. Non-limiting examples of morphological and functional abnormalities include physical deterioration and/or death of neural cells, abnormal growth patterns of neural cells, abnormalities in the physical connection between neural cells, under- or over production of a substance or substances, e.g., a neurotransmitter, by neural cells, failure of neural cells to produce a substance or substances which it normally produces, production of substances, e.g., neurotransmitters, and/or transmission of electrical impulses in abnormal patterns or at abnormal times. Neurodegeneration can occur in any area of the brain of a subject and is seen with many disorders including, for example, Amyotrophic Lateral Sclerosis (ALS), multiple sclerosis, Huntington's disease, Parkinson's disease, and Alzheimer's disease.

As used herein, the term "reduce" refers to inhibit, suppress, attenuate, diminish, arrest, or stabilize a symptom or the phenotypic expression of a neurodegenerative disease, disorder, or condition. It will be appreciated that, although not precluded, treating a disease, disorder or condition reduces the symptoms or phenotypic expression, but does not require that the disease, disorder, condition or symptoms associated therewith be completely eliminated or cured.

As used herein, the terms "prevent," "preventing," "prevention," "prophylactic treatment" and the like refer to reducing the probability of developing a disease, disorder, or condition or severity of onset in a subject, who does not have, but is at risk of or susceptible to developing a disease, disorder, or condition. Thus, in some embodiments, an agent can be administered prophylactically to reduce the risk or severity of the onset of a disease, disorder, or condition, or to prevent the recurrence of a disease, disorder, or condition.

As used herein, the term "disease" or "disorder" refers to any alteration in state of the body or of some of the organs, interrupting or disturbing the performance of the normal functions in a subject As used herein, the term "X-linked" refers to of, relating to, or characterized by genes located on the X-chromosome.

As used herein, the term "X-chromosome inactivation" is a process by which one of the two copies of the X chromosome present in female subjects is inactivated.

As used herein, a "whole genome sequence", or WGS (also referred to in the art as a "full", "complete", or entire" genome sequence), or similar phraseology is to be understood as encompassing a substantial, but not necessarily complete, genome of a subject. In the art the term "whole genome sequence", or WGS is used to refer to a nearly complete genome of the subject, such as at least 95% complete in some usages. The term "whole genome sequence", or WGS as used herein does not encompass "sequences" employed for gene-specific techniques such as single nucleotide polymorphism (SNP) genotyping, for which typically less than 0.1% of the genome is covered. The term "whole genome sequence", or WGS as used herein does not require that the genome be aligned with any reference sequence, and does not require that variants or other features be annotated. The term "whole genome sequencing" refers to determining the complete DNA sequence of the genome at one time.

As used herein the term "whole exome sequencing" refers to selective sequencing of coding regions of the DNA genome. The targeted exome is usually the portion of the DNA that translates into proteins, however regions of the exome that do not translate into proteins may also be included within the sequence.

As used herein the term "whole transcriptome sequencing" refers to determining the expression of all RNA molecules including messenger RNA (mRNA), ribosomal RNA (rRNA), transfer RNA (tRNA), and non-coding RNA.

As used herein the term "high-throughput screening" refers to a process for scientific experimentation especially relevant to the fields of biology and chemistry. Through a combination of modern robotics and other specialized laboratory hardware, it allows a researcher to effectively screen large amounts of samples simultaneously.

As used here in the term "library" is used in its art-recognized sense, that is a collection of nucleic acid molecules (RNA, cDNA or genomic DNA) obtained from a particular source being studied, such as a certain differentiated cell, or a cell representing a certain species (e.g., human).

As used herein the term "probe," refers to a nucleic acid that is complementary to a nucleotide sequence of interest.

As used herein, the term "genome(s)" means the hereditary information of an individual typically encoded in nucleic acids, either DNA, or RNA, and including both genes and non-coding sequences. The genome may refer to the nucleic acids making up one set of chromosomes of an organism (haploid genome) or both sets of chromosomes of an organism (diploid genome) depending on the context in which it is used.

As used herein, the term "chromosome" refers to the support for the genes carrying heredity in a living cell, including DNA, protein, RNA and other associated factors. In a normal diploid human cell of a female, there are 22 types of autosomal chromosomes and two X chromosomes. In a normal diploid human cell of a male, there are 22 types of autosomal chromosomes and two types of sex chromosomes, chromosomes X and Y.

As used herein, the term "single nucleotide polymorphism(s) or SNP(s)" means a polymorphic site at which the sequence variation is caused by substitution of a single base at a specific position. SNPs refer to nucleotide variations at a defined genomic position among a population. A SNP within a coding region, in which both forms lead to the same protein sequence, is termed synonymous; if different proteins are produced they are non-synonymous. SNPs may have consequences for gene splicing, transcription factor binding, or the sequence of non-coding RNA, for example, and/or may indicate the haplotype of the organism.

As used herein the term "haplotype" refers to a set of nucleotide sequence polymorphisms or alleles present on a single maternal or paternal chromosome, usually inherited as a unit.

As used herein the term "integrated" refers to a combination or coordination of otherwise different elements to provide a harmonious and interrelated whole, whether physically or functionally.

As used herein the term "phasing" or "phased alleles" refers to the distribution of the particular alleles on a single chromosome. Accordingly, the "phase" of two alleles can refer to a characterization or determination of whether the alleles are located on a single chromosome or two separate chromosomes (e.g., a maternally or paternally inherited chromosomes). Unless otherwise stated, "haplotype" and "phased alleles" are considered synonymous.

As used herein the term "allele-specific," when used in reference to nucleic acid sequences, such as oligonucleotides and primers, means that a particular position of the nucleic acid sequence is complementary with an allele of a target polynucleotide sequence.

The present invention relates to processes and kits for characterizing and screening for the existence or predisposition to X-linked disorders and/or X-linked disorders associated with changes in X-chromosome inactivation. The present invention also relates to methods of treating a subject having X-linked disorders and/or X-linked disorders associated with changes in X-chromosome inactivation or a predisposition for X-linked disorders and/or X-linked disorders associated with changes in X-chromosome inactivation In one aspect, the present invention provides an integrated high throughput sequencing process to identify an X-linked disorder in a subject. The process typically comprises obtaining a biological sample from the subject comprising nucleic acids; isolating nucleic acids from the biological sample; performing whole genome sequencing or whole exome sequencing by next generation sequencing of the isolated nucleic acids; performing whole transcriptome sequencing by next generation sequencing of the isolated nucleic acids; and identifying at least one genomic or functional biomarker associated with a phenotype of the X-linked disorder, thereby.

In one specific aspect, the invention is directed to a process of characterizing X chromosome inactivation (XCI) in a female subject. The process typically comprises the steps of:

(a) obtaining a first biological sample comprising nucleic acids from the subject, a second biological sample comprising nucleic acids from the biological mother of the subject, and a third biological sample comprising nucleic acids from the biological father of the subject;

(b) isolating the nucleic acids from the first biological sample, the second biological sample, and the third biological sample;

(c) performing whole genome sequencing or whole exome sequencing by next generation sequencing of the isolated nucleic acids from the second biological sample, and the third biological sample;

(d) performing whole transcriptome sequencing by next generation sequencing of the isolated nucleic acids from the first biological sample;

(e) identifying from the whole genome sequencing or whole exome sequencing at least one X-linked variant allele wherein the subject is heterozygous for the at least one X-linked variant allele; and (f) determining from the whole transcriptome sequencing an X-linked variant allele frequency for the at least one X-linked variant allele in the subject by comparing expression of the at least one X-linked variant allele from the biological mother of the subject to expression of the at least one X-linked variant allele from the biological father of the subject, thereby characterizing the XCI in the female subject. Advantageously, in a preferred embodiment, the step of whole transcriptome sequencing is performed simultaneously with step (c) and comprises whole mRNA sequencing.

In a particular embodiment, the process also comprises performing whole genome sequencing or whole exome sequencing by next generation sequencing of the isolated nucleic acids from the first biological sample.

The invention is also directed to a specific process of identifying an X-linked disorder in a female subject. The process generally comprises:

(a) characterizing X chromosome inactivation (XCI) in the female subject according to the process described above; and (b) identifying an X-linked disorder in the female subject if the X-linked variant allele frequency is substantially skewed, wherein the X-linked variant allele frequency is substantially skewed if expression of the X-linked variant allele from the biological mother of the subject compared to expression of the X-linked variant allele from the biological father of the subject differs by at least a ratio of at least 60:40; 65:35; 70:30; 75:25; 80:20; 85:15; 90:10; 95:5; or 98:2. The X-linked disorder identified may be, at least partially, caused by a change in mode and magnitude of XCI.

In a particular aspect of the invention, the process optionally includes the step of simulating RNA sequencing reads in silico from chromosome-wide heterozygous SNP alleles of the sample and calculating allelic skewness ratio by analysis of phased or unphased chromosome-wide heterozygous SNP variant transcripts from the simulated data. The simulation of RNA sequencing in silico typically comprises:

(a) introducing nucleotide changes into a reference chromosome by selecting a number of chromosome wide SNPs from a sample;

(b) separating randomly the SNPs from the reference chromosome of interest into two groups, one group analogous to variant alleles on maternal chromosome referred to as pseudo-maternal variant SNPs and the other group analogous to variant alleles on paternal chromosome referred to as pseudo-paternal variant SNPs;

(c) introducing the pseudo-maternal and pseudo-paternal variant SNPs into two separate chromosome X files and reducing the two files to greater than 500 bp regions that correspond to known transcripts according to human genome annotation *Homo sapiens* to obtain two separate transcriptome files;

(d) generating paired reads mapping to the two separate transcriptome files; and (e) sub-sampling the paired reads randomly in various ratios and merging the randomly distributed reads into a single file.

The invention is also directed specifically to a process of reducing a disease phenotype associated with an X-linked disorder in a female subject. The process typically comprises the steps of:

(a) characterizing X chromosome inactivation (XCI) in the female subject having an X-linked disorder, comprising:
   (i) obtaining a first biological sample comprising nucleic acids from the subject, a second biological sample comprising nucleic acids from the biological mother of the subject, and a third biological sample comprising nucleic acids from the biological father of the subject;
   (ii) isolating the nucleic acids from the first biological sample, the second biological sample, and the third biological sample;
   (iii) performing whole genome sequencing or whole exome sequencing by next generation sequencing of the isolated nucleic acids from the second biological sample, and the third biological sample;
   (iv) performing whole transcriptome sequencing by next generation sequencing of the isolated nucleic acids from the first biological sample;
   (v) identifying from the whole genome sequencing or whole exome sequencing at least one X-linked variant allele wherein the subject is heterozygous for the at least one X-linked variant allele; and
   (vi) determining from the whole transcriptome sequencing an X-linked variant allele frequency for the at least one X-linked variant allele in the subject by comparing expression of the at least one X-linked variant allele from the biological mother of the subject to expression of the at least one X-linked variant allele from the biological father of the subject, thereby characterizing the XCI in the female subject;

(b) identifying a treatable X-linked disorder in the female subject if the X-linked variant allele frequency is substantially skewed, wherein the X-linked variant allele frequency is substantially skewed if expression of the X-linked variant allele from the biological mother of the subject compared to expression of the X-linked variant allele from the biological father of the subject is at least a ratio of 65:35; and (c) treating the X-linked disorder with a gene therapy, a protein replacement therapy, a protein mimetic therapy and/or a small molecule therapy to reduce skewedness of the X-lined variant allele expression, for example if the expression of the X-linked variant allele differs by at least 80:20, the step of treating the X-linked disorder would reduce the skewedness to 75:25 or less. In particular embodiments the X-linked variant allele is a variation in at least one gene selected from the group consisting of VCX3A, HDHD1, STS, VCX, PNPLA4, miR-4767, miR-651.

Next-Generation Sequencing—Whole Genome Sequencing, Whole Exome Sequencing, Whole Transcriptome Sequencing:

Next-generation sequencing (NGS) has dramatically reduced the cost and increased the output of sequencing. Determining the sequence of the entire human genome is referred to as whole-genome sequencing (WGS) and typically costs about three times more than sequencing an individual's exome (the coding sequence of the human genome). The latter is referred to as whole-exome sequencing (WES). WES is generally accomplished using an array that captures the DNA containing the coding sequence from the patient's sample. This captured DNA is then sequenced. An exome is less costly to sequence than a whole genome because the exome represents only about 1% of the genome. NGS is carried out by first breaking the entire genome into small pieces, then attaching those small segments of DNA to special adapters or allowing the pieces to travel through tiny channels in which the sequence of each segment is determined. In NGS millions of these DNA segments from across the genome are sequenced at the same time. NGS devices employ this massively parallel sequencing to deliver very inexpensive sequence data. The result of a sequenced segment is called a 'read'. Each nucleotide of the regions studied will be included in many reads, and, therefore, repeatedly analyzed. The millions of analyzed reads are then used in de-novo assembly or more commonly compared with a reference human genome.

The Reference Human Genome and DNA Variants:

NGS has shown that two unrelated individuals have more than two million differences in their DNA sequence. With so much variability, it is confusing to refer to a 'reference' ('normal') gene or more globally a 'reference' genome. There is no individual's genome that can be called 'reference'. Yet, for convenience, the National Center for Biotechnology Information (NCBI) does maintain and update a reference assembly of the human genome that is derived from many individuals. Any difference from the reference genome maintained by NCBI will be referred to as a variant. When this DNA difference has clinical consequences, it is called a pathogenic variant. When the difference has no effect on the individual, it is called a benign variant. When the effect of the DNA change is unknown, it is called a variant of unknown significance. A more comprehensive classification of variants has been devised.

Analysis of Reads from Next-Generation Sequencing:

In most applications of NGS, after the reads are generated software aligns each read against the reference genome, resulting in many-fold coverage of regions of interest. Once the reads are aligned, the differences between the patient's sequence and the reference sequence are identified. This comparison results in a list of variants (often called a variant table) numbering over two million. In cases in which the reference genome has gaps, NGS reads cannot be aligned and are discarded. In cases in which the reference genome has errors, NGS reads will be assigned to the wrong location and will give misleading results. As NCBI improves the quality of the reference genome, more of the data from NGS is usable and can be accurately assigned. A variety of databases and programs are used to determine the significance of a variant. These databases and programs are growing in number and complexity and have been successfully combined into software packages. Because of the large number of variants, results of this analysis must be combined with the patient's phenotype, possible patterns of inheritance and the potential effect of the variant on the protein to reach an accurate diagnosis. Significantly, the growing number of sequenced human genomes and exomes can help eliminate a large number of benign variants from consideration.

Whole Transcriptome Sequencing:

"Whole Transcriptome Shotgun Sequencing" ("WTSS") also called RNA-seq (RNA Sequencing) is a technology that uses the capabilities of next-generation sequencing to reveal a snapshot of RNA presence and quantity from a genome at a given moment in time. The introduction of high-throughput next-generation DNA sequencing (NGS) technologies revolutionized transcriptomics by allowing RNA analysis through cDNA sequencing at massive scale (RNA-seq). NGS platforms used for RNA-seq are commercially available from four companies—Illumina, Roche 454, Helicos BioSciences and Life Technologies—and new technologies are in development by others. Given the importance of sequencing capabilities, such as throughput, read length, error rate and ability to perform paired reads, for RNA-seq as well as genomic studies, NGS companies are constantly improving their platforms to provide the best sequencing performance at the lowest cost.

In certain embodiment, the whole transcriptome sequencing typically comprises whole mRNA sequencing and is performed simultaneously with the whole genome sequencing or whole exome sequencing. In certain aspects, the process is typically performed on a family trio, wherein the family trio comprises of the subject with the X-linked disorder, the biological mother of the subject and the biological father of the subject. In yet another aspect, the integrated sequencing process provides information on chromosome-wide X-linked heterozygous SNP alleles. In certain other aspect, the X-linked disorder is in part, caused by a change in mode and magnitude of XCI. In a particular embodiment, the mode of XCI is determined by phasing of the chromosome wide X-linked heterozygous SNP alleles of the subject. In another embodiment, the magnitude of XCI is determined in silico by computer simulation of phased or unphased chromosome-wide X-linked heterozygous SNP alleles of the subject or the magnitude of XCI is determined by allele-specific expression analysis of phased or unphased chromosome-wide X-linked heterozygous SNP alleles of the subject that are transcribed into mRNA. In yet other embodiment, the XCI ratio was estimated from phased heterozygous SNPs by beta parametric model and the XCI ratio was estimated from unphased heterozygous SNPs by semi-parametric model. In another embodiment, a combination of the change in mode and magnitude of XCI and the presence of the at least one genomic or functional biomarker is responsible for the phenotype for the X-linked disorder.

In an exemplary aspect, the X-linked disorder is a neurobehavioral condition manifesting at least an emotional instability, attention deficit, or delays in development and learning. In certain embodiment, the biological sample comprises a blood sample or a brain tissue sample from the subject.

In yet other embodiment, the at least one genomic or functional biomarker comprises a large chromosomal deletion and/or amplification. In another embodiment, the large chromosomal deletion and/or amplification is detected by plotting log 2 differences, $$\log 2\left(\frac{\text{\# reads mapping to 100 bp window affected}}{\text{\# reads mapping to all windows in affected}}\right) - \log 2\left(\frac{\text{\# reads mapping to 100 bp window }mom}{\text{\# reads mapping to all windows in }mom}\right)$$

across chromosomes, where a log 2 difference of −1, means a heterozygous deletion in one of the copies, a −2 means a homozygous deletion of both copies, a +1 means a heterozygous copy gain, and a +2 means a homozygous copy gain of the chromosomal region.

In certain aspect, the at least one genomic or functional biomarker comprises an interstitial deletion in a region of the X-chromosome. In one embodiment, the interstitial deletion in the region of the X-chromosome harbors five genes comprising VCX3A, HDHD1, STS, VCX, PNPLA4 and two microRNA genes comprising miR-4767, miR-651, two of the five genes, VCX and VCX3A being associated with neurological dysfunction. In another embodiment, the deletion is a heterozygous 1.7 Mb deletion on the Xp22.31 locus of the X-chromosome between 6,451,600 bp and 8,095,100 bp. In yet another aspect, the deletion is characterized as a de novo mutation by co-segregation analysis of parental genotypes obtained from whole exome sequencing. In certain aspect, source of the de novo interstitial deletion is paternal X-chromosome as identified by phasing of X-chromosome wide heterozygous SNP alleles. In one embodiment, the phasing of the deletion provides mode or direction of XCI as paternal X-chromosome In other aspect, magnitude of XCI or XCI ratio is estimated in silico by computer simulation of phased or unphased chromosome wide X-linked heterozygous SNP alleles or XCI ratio is estimated by allele-specific mRNA expression analysis of phased or unphased chromosome wide X-linked heterozygous SNP alleles that are transcribed into mRNA. In yet other aspect, a combination of mode and magnitude of skewedness or non-randomness in XCI and the interstitial deletion of genes is responsible for the phenotype for the X-linked disorder.

In a second aspect of the invention, the invention comprises of a therapy for preventing or reducing a disease phenotype associated with an X-linked disorder in a subject. The process typically comprises identifying an X-linked disorder in a subject, the process comprising obtaining a biological sample from the subject comprising nucleic acids; isolating nucleic acids from the biological sample; performing whole genome sequencing or whole exome sequencing by next generation sequencing of the isolated nucleic acids; performing whole transcriptome sequencing by next generation sequencing of the isolated nucleic acids; and identifying at least one genomic or functional biomarker associated with the X-linked disorder; and treating the X-linked disorder associated with the identified genomic or functional biomarker with a gene therapy, a protein replacement therapy, a protein mimetic therapy and/or a small molecule therapy.

In certain aspects, the therapy further comprises identifying in the subject a skewed or non-random XCI and treating the subject for correction of effects of the skewed or non-random XCI. In a particular embodiment of the treatment, the genomic or functional biomarker associated with the X-linked disorder is associated with a variation in at least one gene, its transcript or protein product, wherein the gene is selected from the group consisting of VCX3A, HDHD1, STS, VCX, PNPLA4, miR-4767, miR-651.

In a third aspect of the invention, the invention comprises a process of determining skewedness in monoallelic expression of autosomal or X-chromosomal genes in a biological sample. The process preferably comprises subjecting the sample to integrated whole genome sequencing or exome sequencing and whole transcriptome sequencing, and calculating allelic skewedness ratio by allelic specific distribution analysis of phased or unphased chromosome-wide heterozygous SNP alleles that transcribed into mRNA, or simulating RNA sequencing reads in silico from chromosome-wide heterozygous SNP alleles of the sample and calculating allelic skewedness ratio by analysis of phased or unphased chromosome-wide heterozygous SNP variant transcripts from the simulated data. In one embodiment, the simulation of RNA sequencing reads in silico is by a process that comprises introducing nucleotide changes into a reference chromosome of interest from the ESP6500 NHLBI Exome Sequencing Project by selecting a number of chromosome wide SNPs from a sample; separating randomly the SNPs from the reference chromosome of interest into two groups, one group analogous to variant alleles on maternal chromosome referred to as pseudo-maternal variant SNPs and the other group analogous to variant alleles on paternal chromosome referred to as pseudo-paternal variant SNPs; introducing the pseudo-maternal and pseudo-paternal variant SNPs into two separate chromosome X fasta files and reducing the two fasta files to greater than 500 bp regions that correspond to known transcripts according to human genome annotation Homo sapiens GRCh37.62.gtf file so as to obtain two separate transcriptome files; generating 10 million, 100 bp paired reads mapping to the two separate transcriptome files using wgsim 0.3.1-r13 fastq simulator; and sub sampling the 10 million paired reads randomly in various ratios and merging the randomly distributed reads into a single fastq file. In other embodiment, the skewedness in monoallelic expression of genes serves as a marker for identification of autosomal disorders or X-linked disorders.

In a fourth aspect of the invention, the invention comprises of a kit for screening for the existence of an X-linked disorder and/or a predisposition for a X-linked disorder in a subject, the kit comprising at least one genomic or functional biomarker selected from the group consisting of VCX3A, HDHD1, STS, VCX, PNPLA4, miR-4767, and miR-651, and/or at least one biomarker for detecting skewedness or non-randomness of XCI for specifically determining a presence or an absence of the X-linked disorder and/or a predisposition to the X-linked disorder.

This invention is further illustrated by the following additional examples that should not be construed as limiting. Those of skill in the art should, in light of the present disclosure, appreciate that many changes can be made to the specific embodiments which are disclosed and still obtain a like or similar result without departing from the spirit and scope of the invention.

EXAMPLES

Example 1. Materials and Methods

In Silico Experiment:

Estimation of XCI ratio by RNAseq is based on the relative allelic expression of chromosome-wide heterozygous genetic variants that are transcribed into mRNA. Since one copy of the X chromosome is silenced in each cell of a female body, the expression frequency of chromosome-wide variant alleles at heterozygous loci correlate with the proportion of cells actively expressing the X chromosome where the variant is located. Epigenetic modifications, including methylation, cis-, and trans-acting elements, and escape genes can influence the expression of alleles biasing the XCI ratio calculated at a single locus. So chromosome-wide allelic expression analysis strategy can provide a more accurate estimate of overall expression of each X chromosome copy and serve as the basis for XCI ratio measurement. We selected for RNAseq simulation 4996 X chromosome single nucleotide polymorphisms (SNPs) with dbSNP identifier to introduce nucleotide change into a GRCH37.62 reference X chromosome from the ESP6500 NHLBI Exome Sequencing Project. From this list, SNPs were randomly binned (phased) into two groups. Essentially each group was analogous to variant alleles on the two parental X chromosomes, and referred to as pseudo-maternal or pseudo-paternal SNPs from here on. There were 2476 pseudo-maternal and 2520 pseudo-paternal variants, selected respectively. Using seqtk FASTA processing tool the pseudo-maternal and pseudo-paternal nucleotides were introduced into two separate chromosome X fasta files. These two fasta files with their nucleotide changes were analogous to maternal and paternal haplotype. The two files from above were reduced to greater than 500 bp regions that correspond to known transcripts according to human genome annotation Homo sapiens.GRCh37.62.gtf file. The two transcriptome files are analogous to the two X chromosome copies that are expressed in an offspring, each containing alleles with known parental origin. Next we generated 10 million, 100 bp paired reads mapping to the two transcriptome file from above (5 million read1 and 5 million read2) using wgsim 0.3.1-r13 fastq simulator. Command line options for wgsim included, zero indel error rate, an outer distance of 150 bp between the paired reads, a uniform Phred quality score of 40 for each base, and a 0.001% base error rate. The combination of these two pseudo-parental fastq files in various ratios followed by mapping them back to the chromosome X reference, and followed by estimation of allelic expression by read count provides the basis for the estimation of XCI ratio. Essentially, after the two pseudo-parental fastq files each with 10 million reads were generated, seqtk was used to subsample them randomly, and merge each parental set into a single fastq file analogous to the reads obtained through RNA sequencing of an experimental sample. When, for example, XCI ratio of 75:25 was simulated, 7.5 million correctly paired reads were randomly sampled from pseudo-maternal fastq file and 2.5 million were subsampled from pseudo-paternal fastq file and merged. In theory, after alignment and allele count, there would be a 75:25 allelic imbalance in favor of the pseudo-maternal alleles to an overall chromosome wide 75:25 ratio since approximately 75% of reads contain alleles from the pseudo-maternal SNPs. Using this approach we simulated RNAseq reads for 11 expected X inactivation ratios: completely skewed X inactivation (100:0), extremely skewed X inactivation (95:5, 90:10), moderately skewed X inactivation (85:15, 80:20), and random X inactivation (75:25, 70:30, 65:35, 60:40, 55:45, 50:50).

Estimation of XCI Ratio:

Estimation of XCI ratio followed similar steps in both in silico experiment and clinical case. Reads were aligned to human reference genome GRCh37.62 using TopHat2 [21]. Alignment of next generation sequencing data has reference bias that may influence the allelic ratio estimate of SNP alleles. Reduction of bias can be achieved by read alignment to diploid reference incorporating paternal genotype information or by reduction of mapping stringency by increasing the number of mismatches allowed in a read for alignment [22, 23]. In the in silico experiment we allowed 5 mismatches and in the clinical case we allowed 4 mismatches per 100 bp read. Allele counts were obtained by generating a chromosome wide pileup with samtools mpileup command [24]. Bases with Phred quality score >20 were counted in both in silico and clinical experiments. Pileups were parsed by in-house perl script. Next we calculated the allelic ratio at each heterozygous locus, dividing the number of reads mapping to the variant allele with the total number of reads mapping to the locus. After allelic ratio calculation the SNPs were further filtered for quality by following procedure: (1) Filtered out all SNPs that lie within the PAR1 and PAR2 pseudo-autosomal regions as they follow autosomal inheritance and can bias XCI ratio[25] (2) Filtered for high confidence variant loci from exome dataset with a genotype filter score of PASS by GATK VariantRecalibrator [26]. (3) Filtered out all loci without a dbSNP identifier. (4) We selected variant with a minimum of 20× coverage to estimate XCI ratio After filtering we used the phasing of the alleles to estimate XCI ratio. Phasing of X-linked heterozygous variants allows us to evaluate the functional profile of each inherited parental copy. By estimating the parameters (mean, variance) of each copy's allele ratio distribution we can estimate the proportion of cells with maternal or paternal X as active and inactive (e.g. mean allelic ratio of paternal alleles of 65% and mean allelic ratio of maternal alleles of 35% equals and estimated XCI ratio of 65:35). To control for over-dispersion of read count data form RNAseq, we used Beta-binomial model to estimate the parameters of the phased allelic ratio distributions [27-30]. We used the fitdistr module of MASS package in R to obtain the parameters.

We also evaluated XCI ratio without phasing the alleles. When phasing information is unavailable we can lose our ability to define the activity of the parental chromosomes. In this case, the inheritance is unknown and the distribution of allele expression from the two chromosome copies may overlap suggesting similar proportion of cells with one of the parental copies active. However, alleles sampled from the two chromosome copies can have their unique distribution pattern resulting in multi-modal allele distributions. Multi-modal distributions can be understood as a mixture of two or more distributions and thus mixture models based on the expectation maximization (EM) algorithm may be used to estimate the parameters of each component or mode of the distribution. The problem with normal mixture modeling is that the number of components in the data set can greatly affect outcome and advised to account for prior modeling. Semi-parametric (SP) model, however, has no assumptions about the modality or the normality of the data and can also approximate the parameters of each component in a data distribution. In estimation of the inactivation status of the X chromosomes, the mean allelic ratios estimated by the SP test can directly correlate to the proportion of cells carrying the variant alleles. Thus, allelic expression captured in component 1 and 2 of an allelic distribution can be thought of as indicators of proportion of activity of parentally inherited chromosomes in the tissue source. Semi-parametric (SP) method is motivated by the fact that the choice of a parametric family may not always be evident from the distribution of the data, as is the case in over-dispersed and heavy-tailed distributions [31]. We applied Bordes et al. stochastic expectation-maximization algorithm for estimating semi-parametric model parameters for unphased data [32]. The mean of the estimated component distributions were utilized as the expression status of each inherited chromosomes but were blind to the origin of alleles and applied to define XCI ratio.

Clinical Case—RNA and DNA Collection:

Whole blood was collected from father, mother, and child into EDTA Blood tubes and PAXgene RNA tubes. Genomic DNA was isolated with DNeasy Blood & Tissue Kit (Qiagen, Germantown, Md.), and total RNA was isolated from PaxGene RNA tubes using PAXgene Blood miRNA kit (Qiagen, Germantown, Md.) following manufacturer's suggested protocol. Patients were consented and enrolled with the approval of the institutional review board to the Center for Rare Childhood Disorder program at the Translational Genomics Research Institute.

Exome and RNAseq Library Preparation and Sequencing:

Exome capture and library preparation was performed with 2 μg of input genomic DNA for each participant using the TruSeq DNA sample preparation kit v2 and the TruSeq Exome Enrichment kit v2 (Illumina, San Diego, Calif.) following manufacturer's guidelines. Briefly, randomly fragmented genomic DNA sample is indexed with a short oligonucleotide identifier followed by pooling of these indexed DNA samples, now called libraries into pooled libraries. These pools are subjected to a two-round, solution based target capture of the approximately 60 Mb of protein coding, 5', and 3' UTR sequences of the genome by biotin labeled synthetic bait oligos. The captured exome DNA fragments are fished from this mixture of target and non-target fragments by streptavidin magnetic beads. After the non-hybridized DNA is washed away and the captured exome fragments are disassociated from the probes, the captured target fragments were enriched by PCR. The three indexed libraries were sequenced as part of a pool of 6 libraries on two lanes of a HiSeq2000 v3 flowcell using version 3 of Illumina's multiplexed paired-end sequencing chemistry for 101 bp read length (Illumina, San Diego, Calif.).

RNA library preparation was performed for each study participant from 1.5 μg of total RNA using Illumina TruSeq RNA Sample Prep Kit v2 according to manufacturer's instructions (Illumina, San Diego, Calif.). Briefly, mRNA is captured from total RNA using polyA associated magnetic beads, then mRNA is transcribed into cDNA, and cDNA is thermally fragmented. The fragmented cDNA is then indexed with unique identifier oligonucleotide sequences, and enriched by PCR into libraries. These libraries are then pooled and loaded onto a flowcell for sequencing. The three indexed libraries were sequenced as part of a final pool of 4 libraries on a single lane of a HiSeq2000 v3 flowcell using version 3 of Illumina's multiplexed paired-end sequencing chemistry for 101 bp read length (Illumina, San Diego, Calif.).

Exome Data Processing:

Binary base calls in the form of .bcl files were generated by the Illumina HiSeq2000 RTA module during sequencing and were converted to compressed fastq files separated for each index using CASAVA 1.8.2 (Illumina, San Diego, Calif.). Quality filtered fastq files were aligned to NCBI reference GRCh37.62 with BWA 0.6.2-r126 [33]. Binary alignment files were converted and coordinate sorted into the standard BAM format using samtools 0.1.18 [24]. Aligned reads were realigned around short insertion and deletions and duplicate reads were filtered using Picard 1.79. This followed aligned base quality recalibration with GATK 2.2 [26]. Flowcell lane level sample BAMs were then merged with Picard 1.79 if samples were sequenced across multiple lanes. Variant calling was done by UnifiedGenotyper and genotype quality recalibrated using VariantRecalibrator described in the best practice methods of GATK 2.2 [34].

RNAseq Data Processing:

After bcl conversion lane level fastq files were appended together if samples were run across multiple lanes. These fastq files were then aligned to human reference genome GRCh37.62 using ensembl.63.genes.gtf of annotated, known transcripts with TopHat2 [21]. Aligned reads were assembled into transcripts with Cufflinks 2.0.2 using known transcript annotation in ensembl.63.genes.gtf as guide and we used annotated high abundance transcript annotation of ribosomal RNA and mitochondrial genes in an ensembl.63.genes.MASK.gtf mask file to reduce dataset. Post transcript assembly, Cufflinks was used to calculate the relative concentration of each annotated transcript by assigning an FPKM value (Fragments Per Kilobase of transcript per Million mapped reads) to each gene and transcript [35].

Calculation of Physical Coverage:

To determine the boundaries of the interstitial deletion on X, we obtained sequence read counts across the X chromosome in a 100 bp sliding window for the mother and child using previously described methods [6]. This script uses the samtools package to parse a bam file containing the sequenced reads of the exome sequencing experiment for affected child and mother [24]. The algorithm uses a sliding window across the selected chromosome in 100 bp length, and for each read mapping within the window finds its mate pair and fills in the gap between the read pairs, then counts this gapped read as one read mapping within the window. This raw read count per 100 bp window is then normalized by dividing the raw read count with the total reads mapping to the sum of sliding windows. Next, the normalized coverage in each window is transformed to log 2 scale in both the mother and child and log 2 transformed normalized read count is deducted from each other as described here:

$$\log2\left(\frac{\text{\# reads mapping to 100 bp window affected}}{\text{\# reads mapping to all windows in affected}}\right) - \log2\left(\frac{\text{\# reads mapping to 100 bp window } mom}{\text{\# reads mapping to all windows in } mom}\right)$$

Plotting log 2 differences across chromosomes allows detection of large chromosomal deletions and amplifications, where a log 2 difference of −1 means a heterozygous deletion in one of the copies, a −2 means a homozygous deletion of both copies, a +1 means a heterozygous copy gain, and a +2 means a homozygous copy gain of the chromosomal region.

Genotype Phasing:

While any given SNP or indel could be potentially causative towards a disease phenotype, SNPs could also be used as markers for phasing. In this study, we were interested in phasing the deletion and the X inactivation skewing. We refer to the process of phasing as determining the parent-of-origin of a molecular variant (i.e., a heterozygote SNP or mRNA transcript containing a SNP), recognizing that phasing can have broader meanings. In our analyses, we use SNPs as markers to phase a genetic interval or region, where the interval could be a deletion, gene transcript, or chromosome. For example, if the proband is "A/T" for a SNP, the mother is "A/T" and the father is "A/A", we can determine the "T" allele is from the mother. Larger events can also be phased by examining SNP genotypes contained within the larger event (i.e., a deletion); however, this requires that one recognize that SNP genotypes should be recoded to match their ploidy. For example, males containing a single X chromosome should be understood to be "A" and not "A/A". Likewise, SNPs within a deletion should be understood to be "T", rather than "T/T".

Skewed Expression Analysis:

To determine the extent of biased gene expression suggested by the HUMARA assay, expression analysis was performed on those SNVs that were called heterozygous in the child's exome and correct phasing of the alternative allele could be determined. First, Genome Analysis Toolkit's UnifiedGenotyper was used one the exome data to identify potential short nucleotide variations (SNV) among the family members that are different from reference genome. This resulted in a multi-sample VCF file with 84,366 called loci. These loci were recalibrated and filtered for quality using GATK VariantRecalibrator, so only loci with a minimum base quality of 10 and reads with the minimum mapping quality of 10 were considered for downstream analysis. From the recalibrated, whole-exome SNV call set there were 1,729 that mapped to chromosome X, of which 901 was call heterozygous in the affected child. 670 heterozygous SNVs were correctly phased, requiring father to be an obligate homozygote for either reference or alternative allele and mother being either a homozygote or heterozygote. Those loci were also filtered out where paternal and maternal homozygous genotype was the same. Essentially, if child was 011 heterozygote and dad was 010 homozygous reference, mother had to be a 111 homozygous alternative genotype or 011 heterozygote. In this case the child had to inherit the reference allele from the father (0) and the alternative allele (1) from the mother. Using the abundance of mRNA determined by RNAseq we quantitated the frequency of the maternally expressed alternative allele in above example.

Allele counts were obtained by generating a transcriptome-wide pileup from the child's RNA-seq accepted hits-.bam file using samtools version 0.1.18 with the mpileup command. Pileup was parsed to count the number of times the reference and alternative allele were sequenced across each pileup locus using an in-house perl script. Next, the list of parsed loci, across the X chromosome, were cross-referenced with the phasing information to obtain allele counts for paternally inherited SNVs and for maternally inherited SNVs. Following this, the frequency of the alternative allele was calculated at each heterozygous locus and filtered for only those sites that had a minimum of 10 fold read coverage and passed false discovery analysis (marked with PASS in recalibrated exome VCF file). (FIG. 1 and Table 1). The ratio of biallelic expression of the maternally inherited alternative allele compared to the paternal reference allele gave an estimate of the ratio of cell population expressing the maternal gene where the variant allele resides compared to the cells that express the paternal same gene where the paternally inherited reference allele resides.

TABLE 1

Phased Allele-Specific Expression of Parental SNPs.

| Status | SNV Origin | Phased heterozygous SNVs | Expressed in blood | Read depth >10 | Mean SNV allele frequency | STDEV |
|---|---|---|---|---|---|---|
| Affected female: | paternal | 362 | 171 | 71 | 24.65 | 13.54 |
|  | maternal | 308 | 134 | 56 | 78.88 | 15.00 |
| Unrelated female: | paternal | 1150 | 549 | 122 | 43.76 | 13.94 |
|  | maternal | 1354 | 681 | 115 | 55.60 | 13.17 |

Example 2. Estimation of XCI Ratio from Simulated Data

Figure 2:
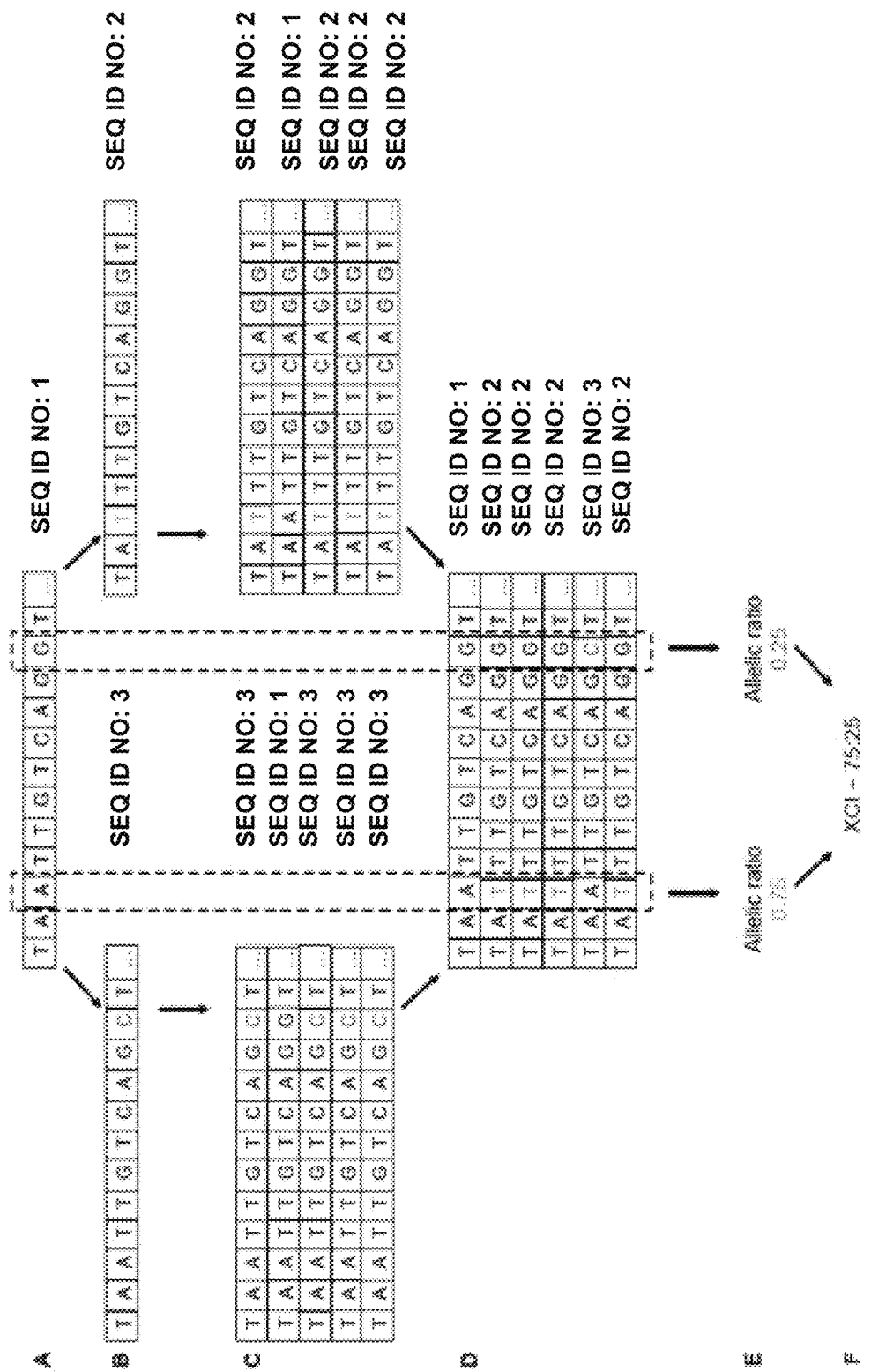
FIG. 2 depicts schematic view of estimation of XCI ratio from simulated read count data. From a reference transcriptome (A), two haplotypes are simulated with their private variants (B) and used as phase information. Sequence read simulator generates reads with error attributes using the two haplotypes as reference (C). The reads from both read simulations are merged and aligned back to the original reference (D). Counting the number of reads mapping to each allele using the phase information, we can estimate the allelic ratio of mapped variant alleles (E). XCI is determined by the phased, allelic ratios of multiple SNP markers (F).
Figure 3:
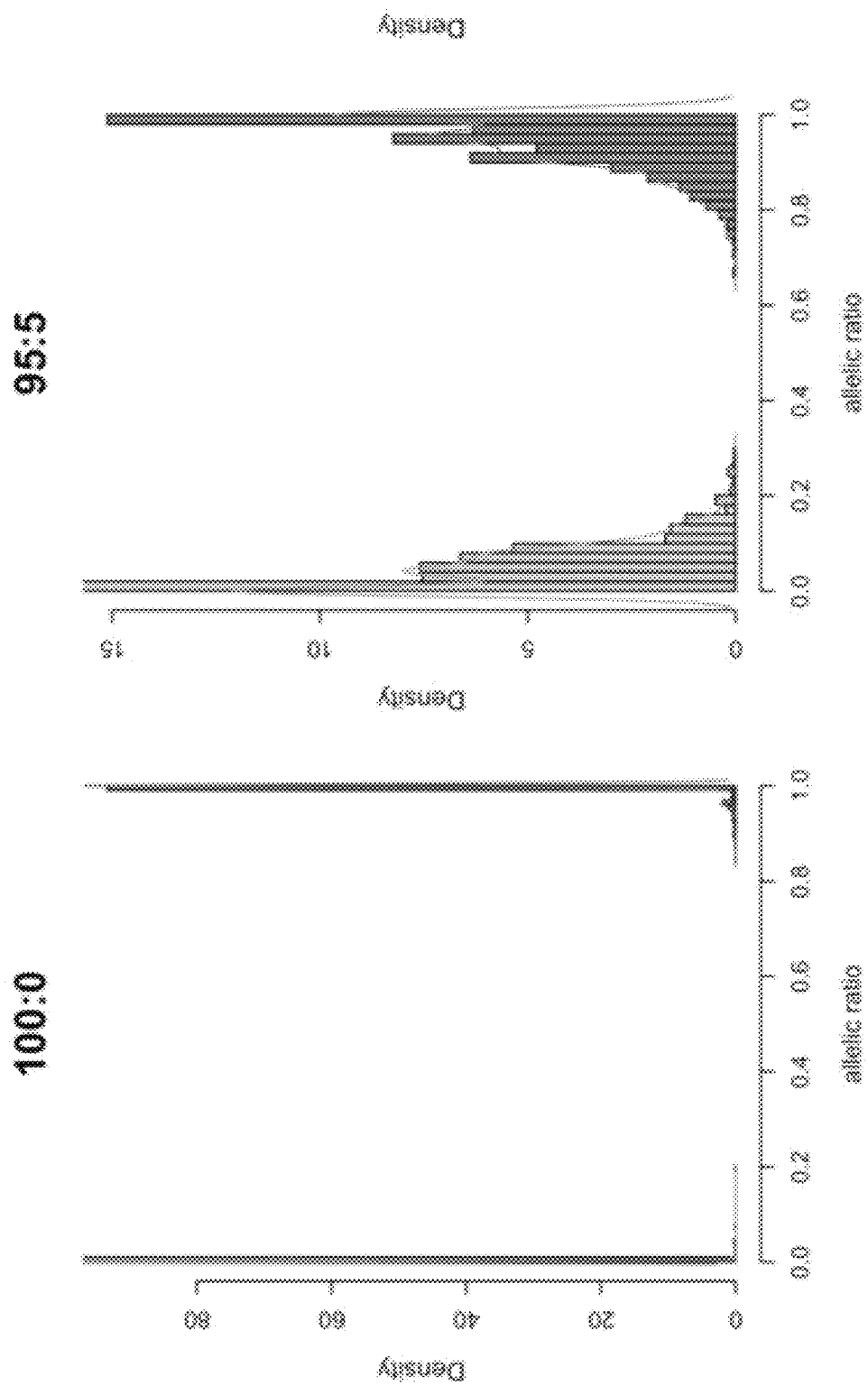
FIG. 3 shows phasing and distribution of in silico allelic ratios. Histograms of showing the allelic ratio distribution after each heterozygous SNP in the in silico data is assigned phase. Each heterozygous SNP allele was covered with at least 20 reads. Pseudo-maternal allelic ratios (magenta) and pseudo-paternal allelic ratios (green) in bins of 20. Dark bars indicate SNP ratios that overlap between phased groups. Colored lines are the kernel density estimates of the phased allelic ratio distributions.
Figure 3:
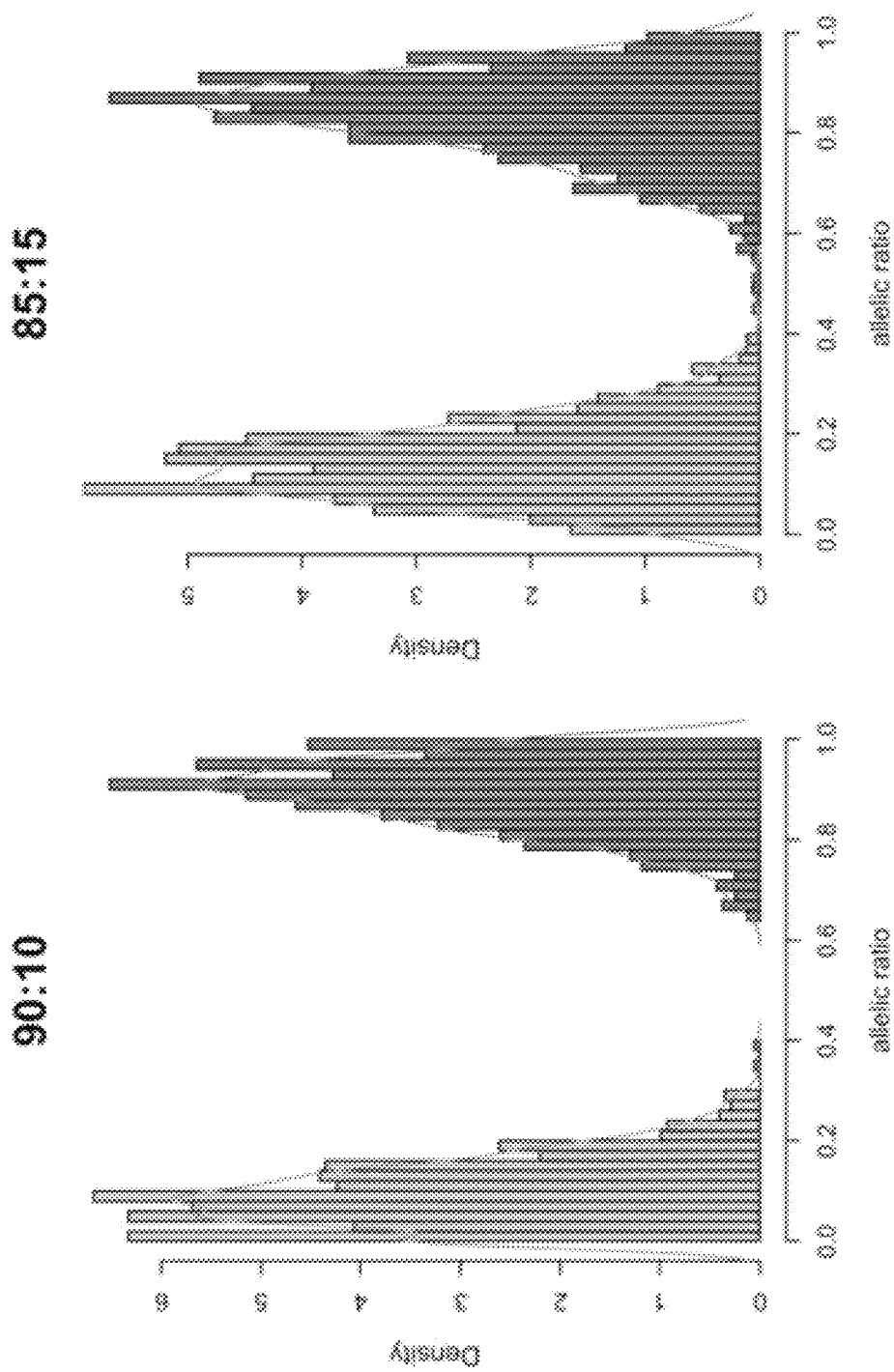
Figure 3:
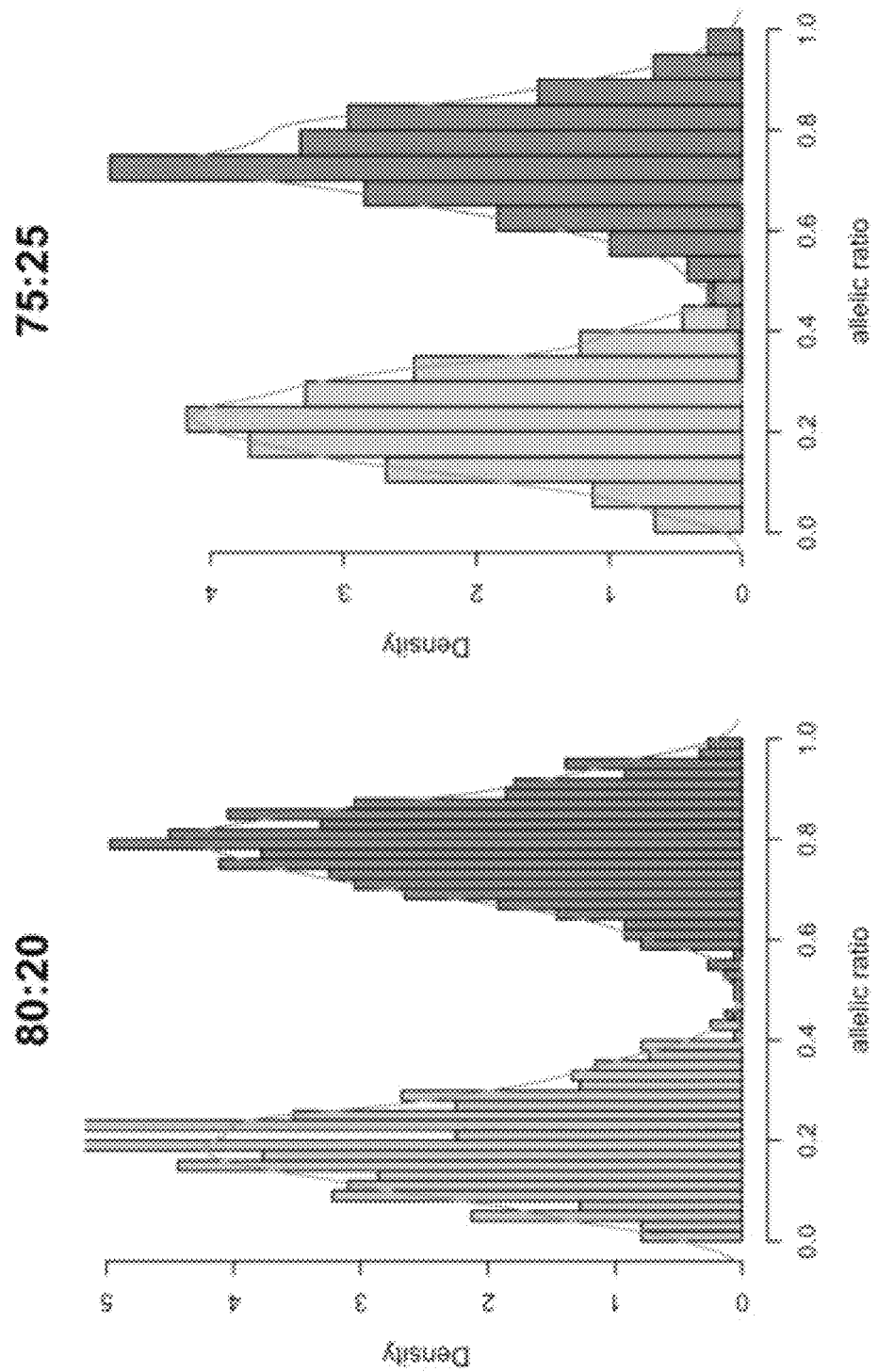
Figure 3:
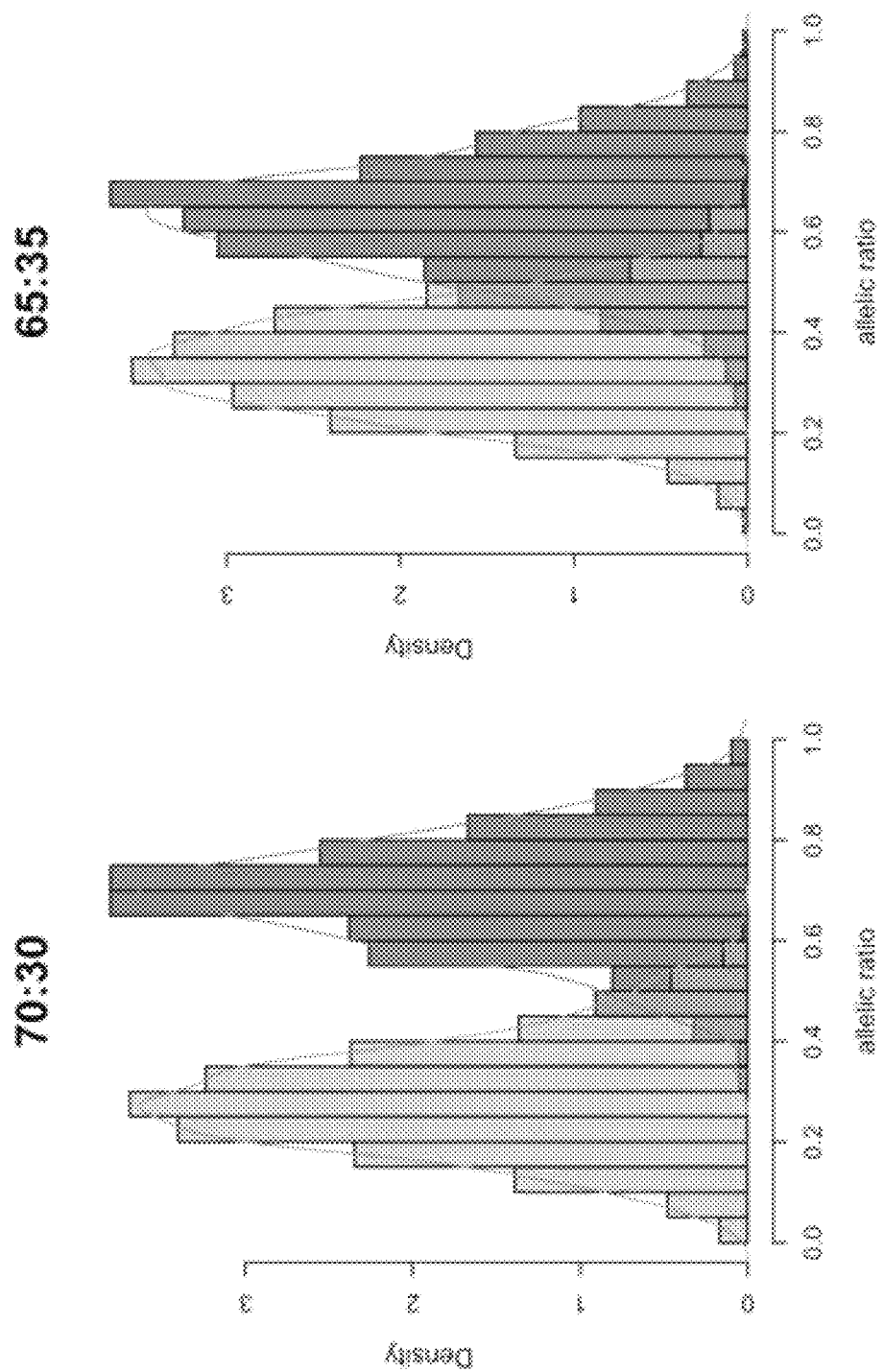
Figure 3:
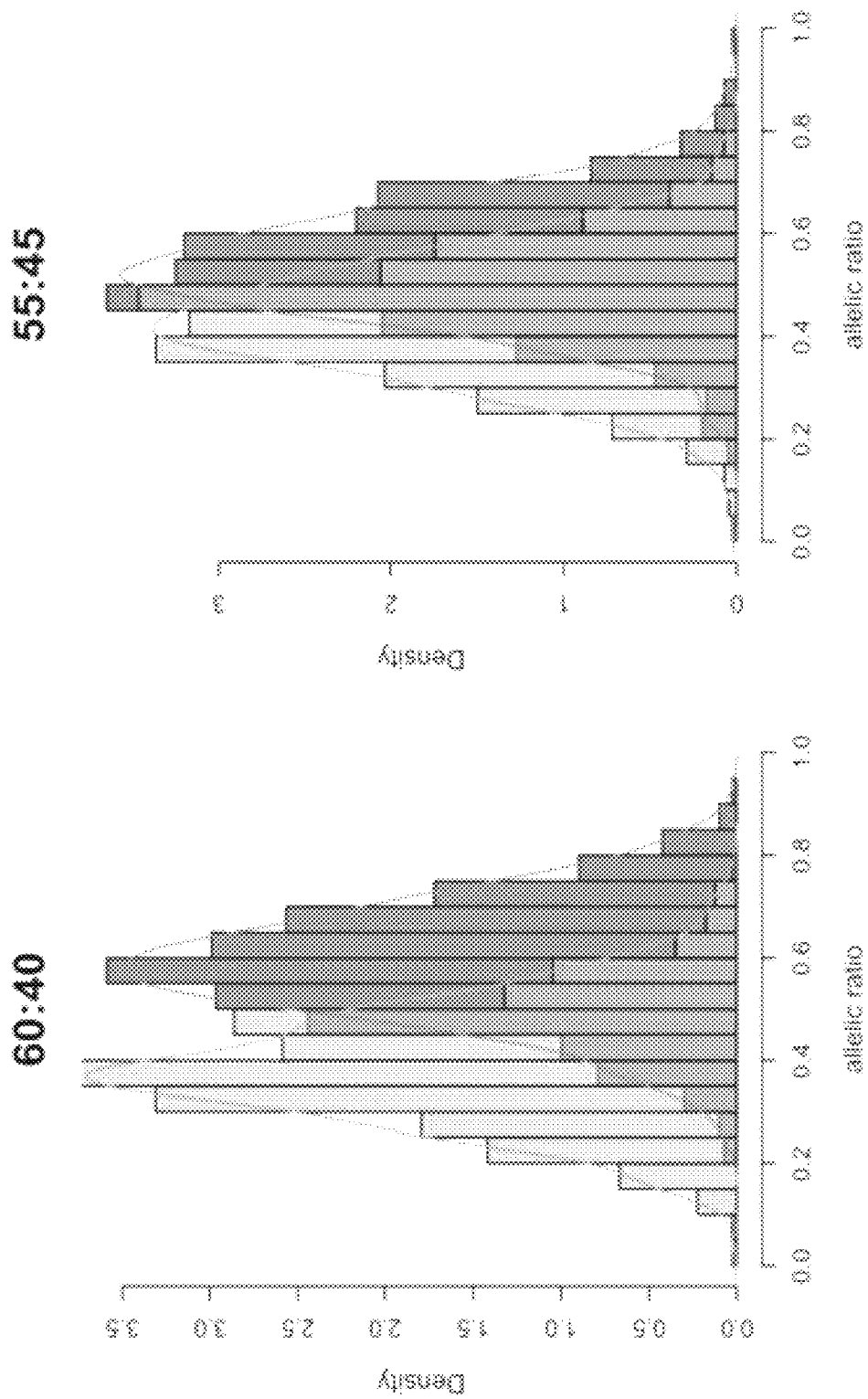
Figure 3:
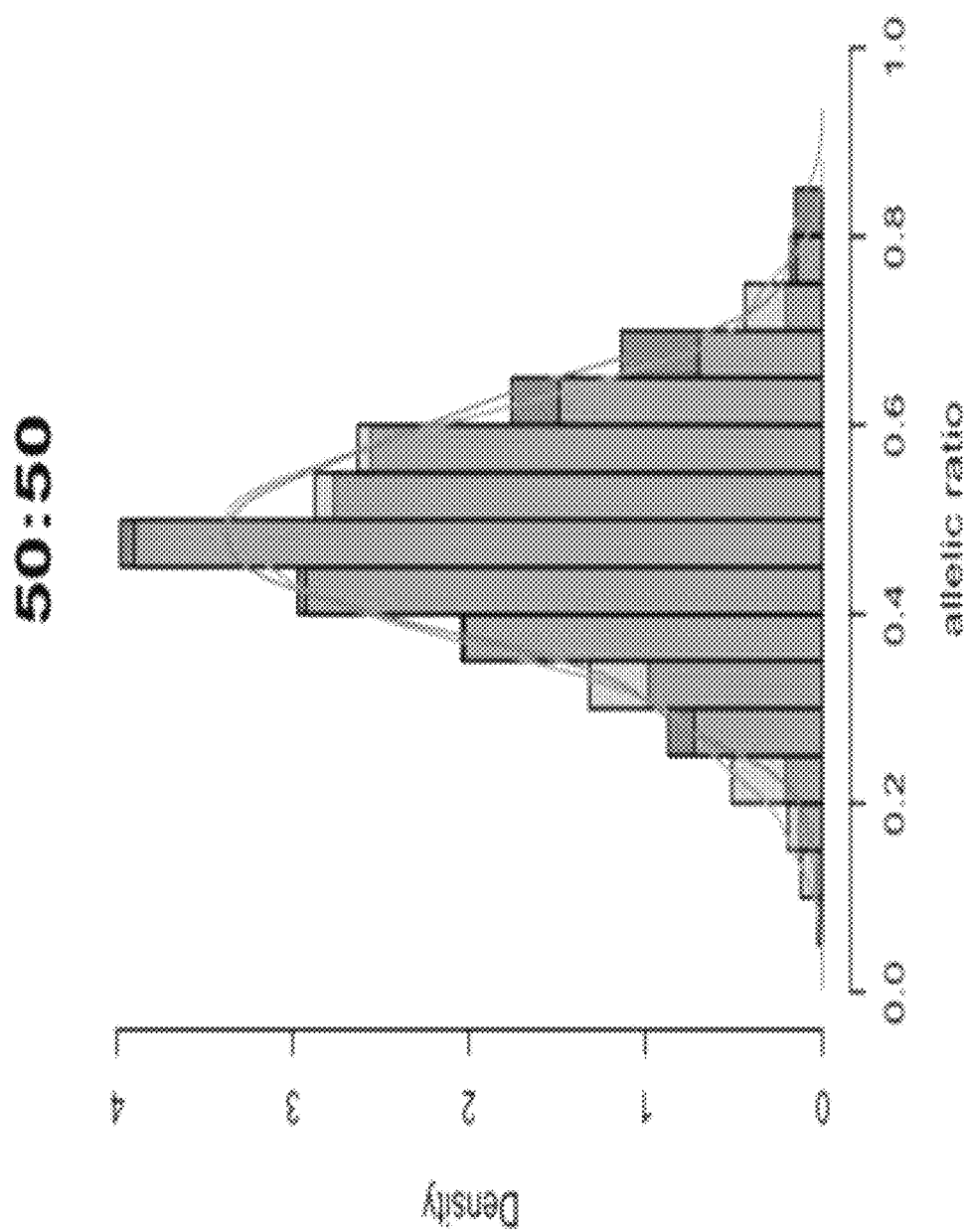

We developed a simulation study for 11 datasets to estimate XCI pattern from paired, RNAseq reads (FIG. 2). For each dataset, more than 4800 loci provided read count information to estimate XCI and on average 1600 SNPs had a minimum read depth of 20. After phasing, the pseudo-maternal and pseudo-paternal allelic distributions were evaluated by beta test to obtain mean ratio of each phased distribution. The distributions showed increased mono-allelic expression from 50:50 random to 100:0 completely skewed XCI (FIG. 3). As expected, at 50:50 XCI ratio, the pseudo-maternal and pseudo-paternal distributions almost completely overlap with their means ratio at around 0.5 indicating bi-allelic expression and suggesting approximately equal expression of both chromosomes (FIG. 3). At each expected XCI ratio, the experimental XCI ratio by beta testing of the phased alleles showed high concordance with expected XCI (Table 2).

TABLE 2

Estimation of XCI ratio of phased data by beta testing. XCI ratio is estimated by the combined mean allelic ratios of the phased X-linked alleles with a minimum coverage of 20 reads. Each expected ratio from complete skewing 100:0 to random X-inactivation was simulated and allelic ratios phased to arbitrarily defined pseudo-maternal and pseudo-paternal alleles. The combination of the mean ratios by beta testing provides final estimate of overall XCI.

| Expected XCI ratio (%) | Pseudo-maternal mean ratio (%) | Standard deviation | Pseudo-paternal mean ratio (%) | Standard deviation | Observed XCI Ratio (%) |
|---|---|---|---|---|---|
| 100:0 | 99.64 | 1.81 | 0.06 | 0.31 | 99.64:0.06 |
| 95:5 | 95.46 | 11.88 | 3.91 | 10.83 | 95.46:3.91 |
| 90:10 | 90.63 | 15.12 | 7.96 | 14.63 | 90.63:7.96 |
| 85:15 | 84.82 | 14.35 | 13.11 | 14.79 | 84.82:13.11 |
| 80:20 | 78.91 | 12.91 | 18.01 | 15.40 | 78.91:18.01 |
| 75:25 | 74.31 | 12.63 | 22.59 | 11.61 | 74.31:22.59 |
| 70:30 | 69.76 | 14.02 | 28.87 | 10.94 | 69.76:28.87 |
| 65:35 | 63.25 | 11.59 | 34.11 | 10.78 | 63.25:34.11 |
| 60:40 | 58.76 | 11.47 | 39.15 | 11.58 | 58.76:39.15 |
| 55:45 | 54.05 | 11.51 | 42.88 | 14.08 | 54.05:42.88 |
| 50:50 | 49.25 | 11.79 | 47.84 | 12.00 | 49.25:47.84 |

Figure 4:
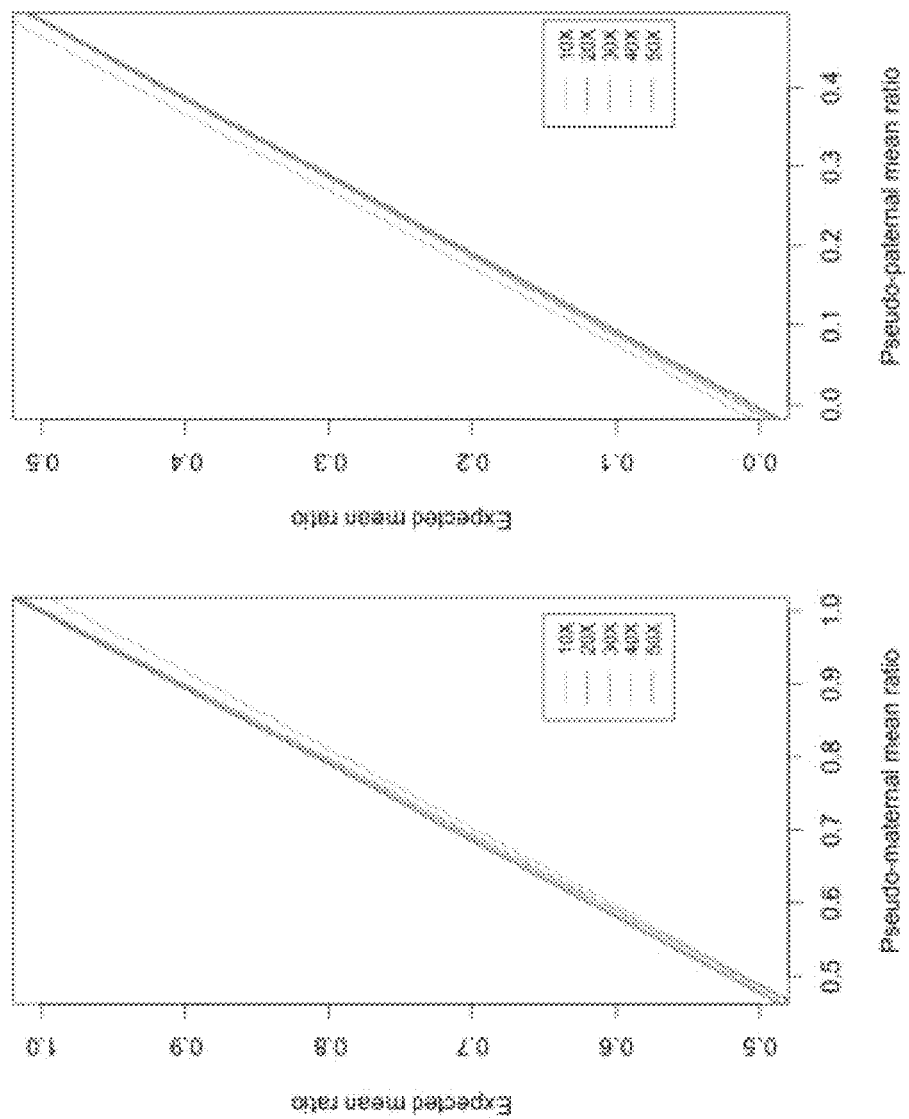
FIG. 4 shows correlation of expected and observed XCI ratios for each phased allelic distributions in terms of sequence coverage. (A) The mean allelic ratio of the pseudo-maternal alleles the in silico data to their corresponding expected allelic ratio. In 70:30 simulation, pseudo maternal alleles have an observed mean allelic ratio of 69.0. (B) The mean allelic ratio of pseudo-paternal alleles from each in silico dataset. In 70:30 simulation, pseudo-paternal alleles have an observed allelic ratio of 27.6. Each color indicates the correlation of observed vs. expected ratios at minimum sequence coverage of 10×, 20×, 30×, 40×, 50×. Pearson correlation coefficient was highest at r>0.9998 above 20× read coverage.
Figure 5:
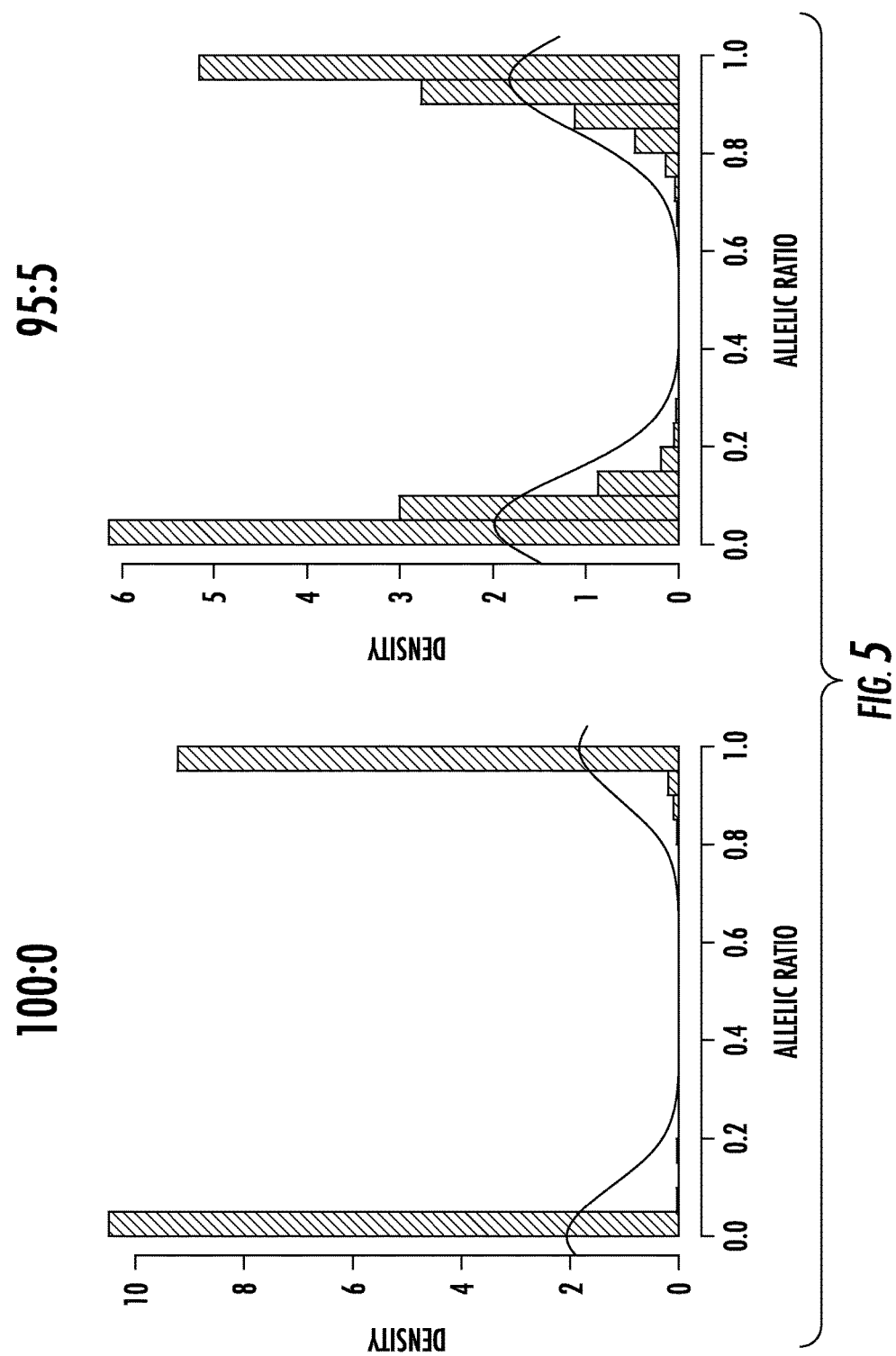
FIG. 5 shows unphased allelic ratio distributions. Histograms showing the allelic ratio distribution after each heterozygous SNP in the in silico experiment when phase is not assigned. Each heterozygous SNP had to be covered with at least 20 reads. Black lines indicate the Gaussian kernel density of unphased allelic ratio distributions. Similar to phased experiments, the shift of distributions from unimodality in random XCI (50:50) toward bi-modality as XCI becomes more skewed towards 100:0 complete skewing.
Figure 5:
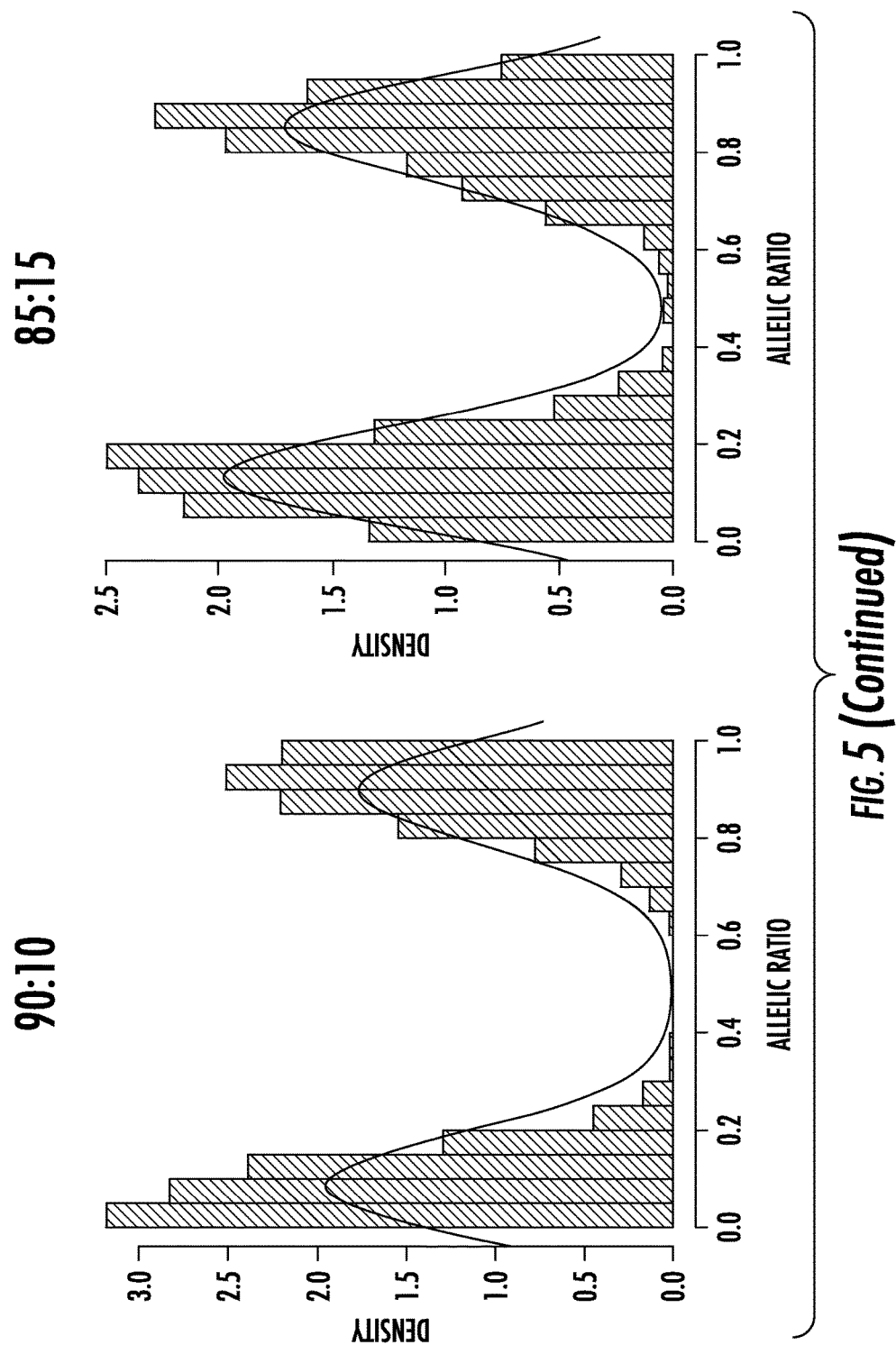
Figure 5:
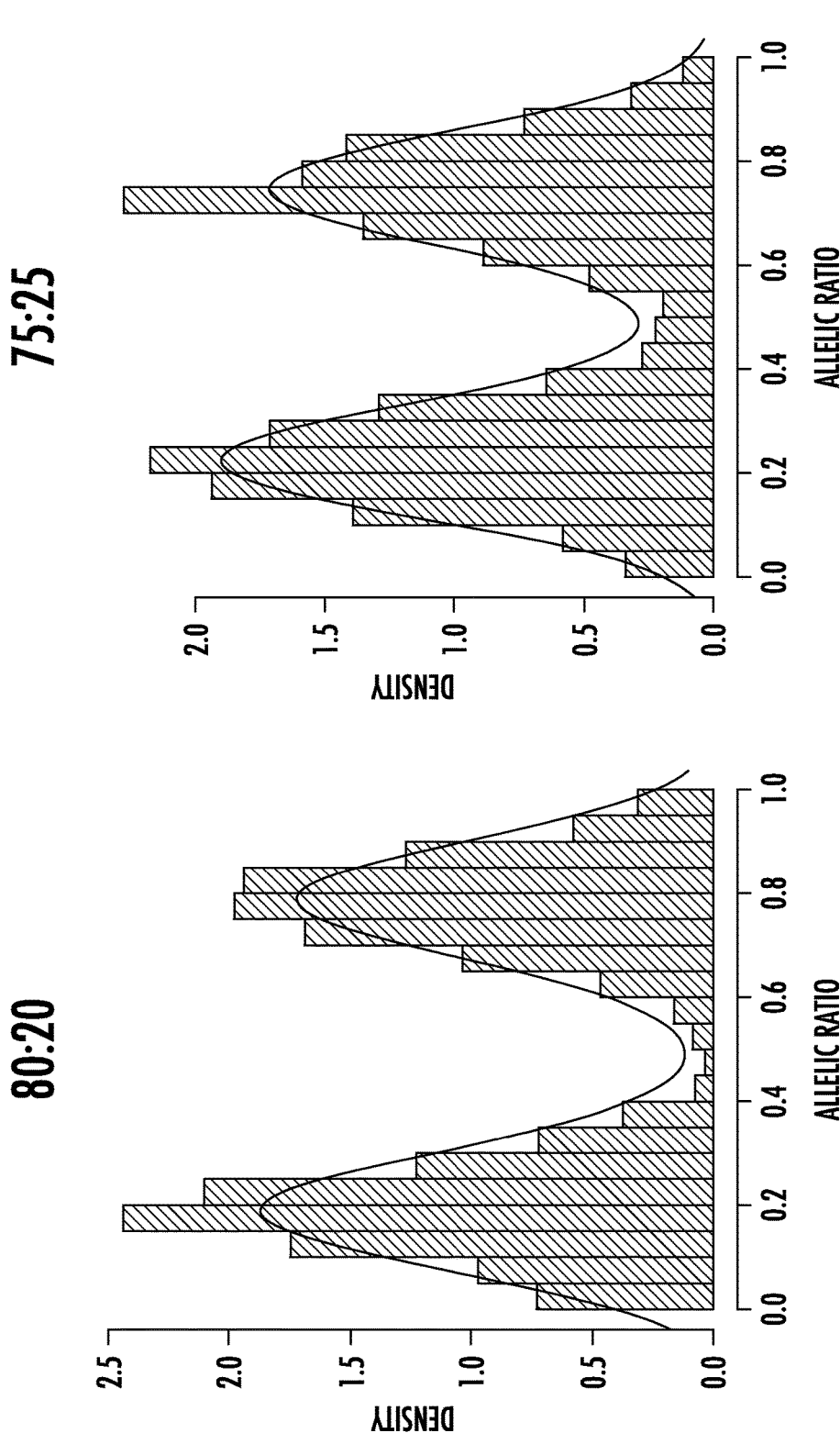
Figure 5:
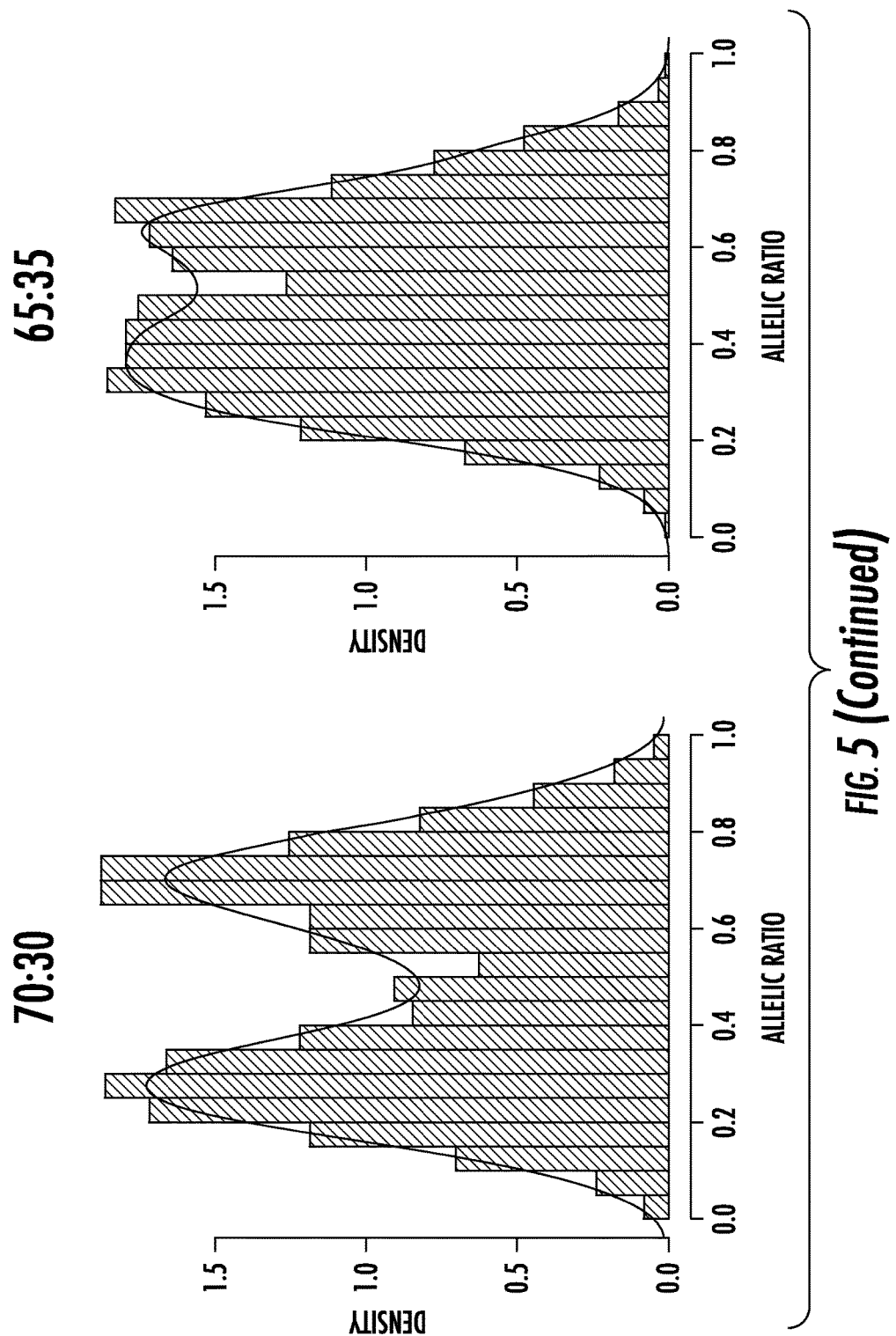
Figure 5:
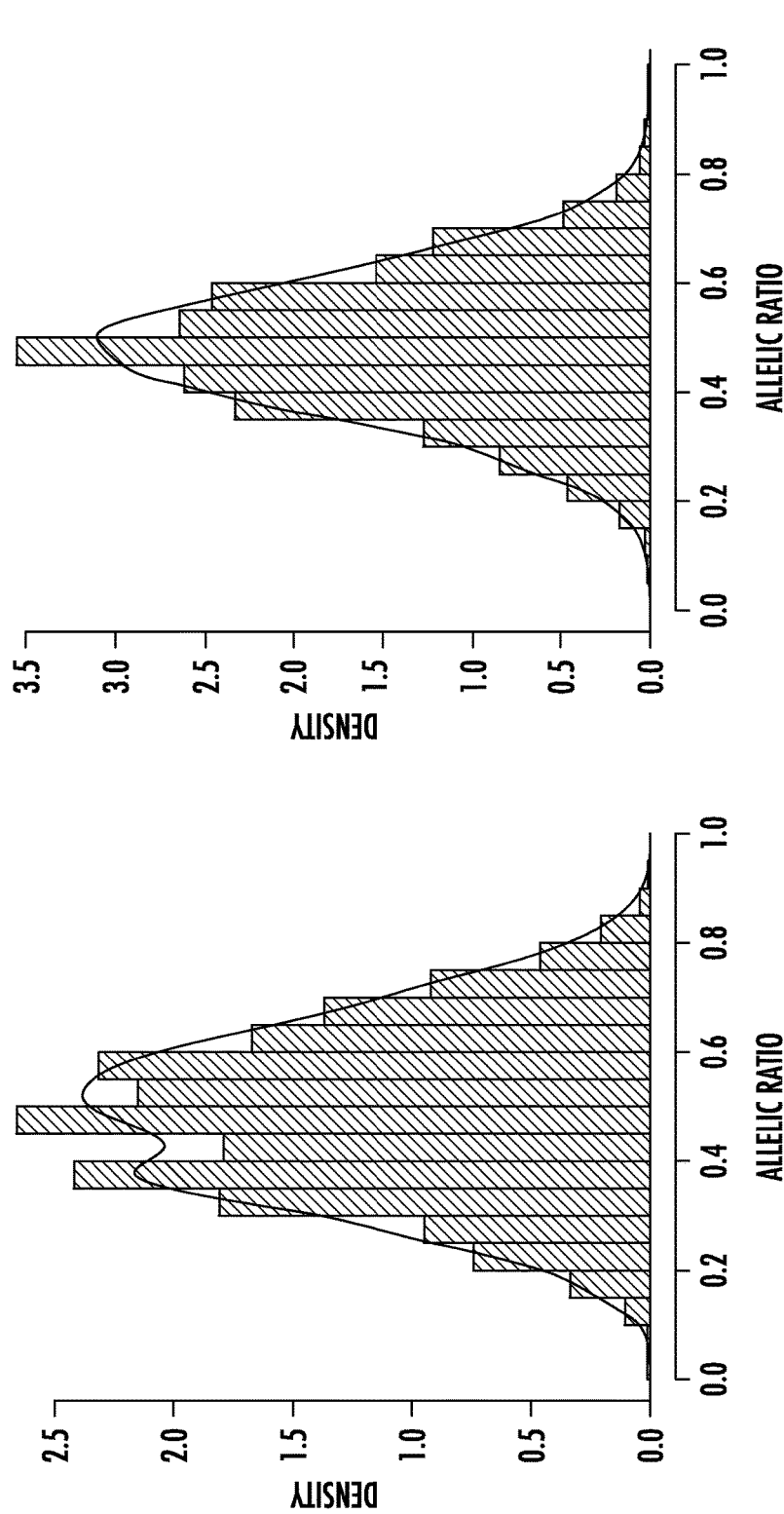
Figure 5:
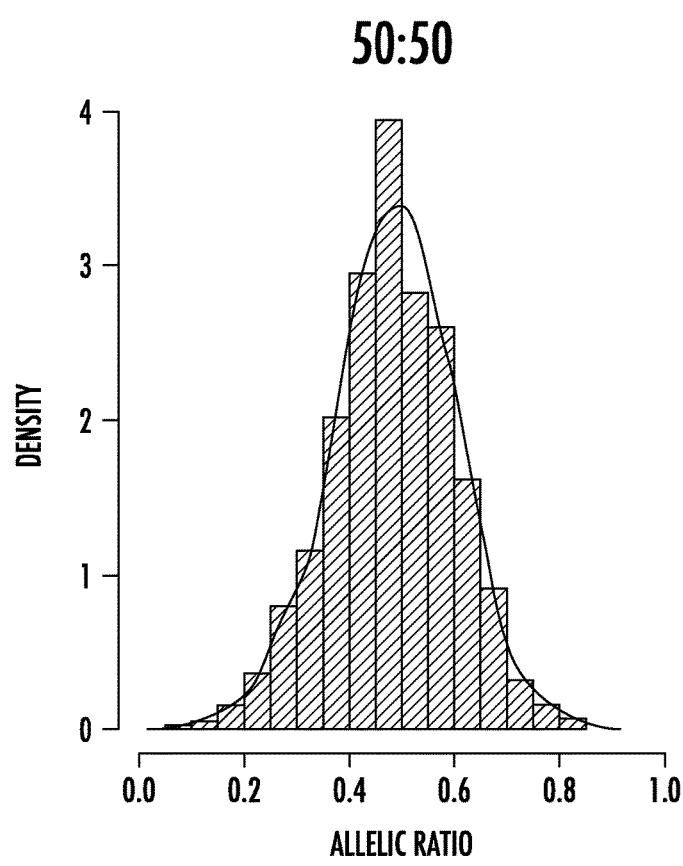

Although we compensated for read mapping bias by allowing 5 mismatches in a 100 bp read, our results show some deviation from the expected mean XCI in each dataset. Since our reads were generated against only known transcripts of 500 bp or longer, some sequence homology between transcripts and the other regions of chromosome X may have resulted on some read bias affecting allelic ratio estimates. As we shift expected allelic ratios from 50:50 random toward completely skewed 100:0, we observed an increased bimodality with the two phases separating into discrete distributions. Coverage analysis indicated high correlation between expected and observed XCI ratios. Although pearson's correlation was above 0.990 from coverage as low as 10×, correlation coefficient converges with expected was achieved at >0.999 above 20× suggesting that as low coverage RNAseq experiments may be used for XCI ratio estimation. (FIG. 4). Unphased allelic ratio distribution followed similar distribution pattern to phased dataset (FIG. 5). Application of semi-parametric model to unphased allelic ratios result in consistent estimation of expected XCI ratios (Table 3).

TABLE 3

Estimated XCI ratio of unphased data by semi-parametric method across 11 in silico experiments.

| Expected XCI ratio | Component 1 mean allelic ration (%) | Standard deviation | Component 2 mean allelic ratio (%) | Standard deviation | Observed XCI ratio |
|---|---|---|---|---|---|
| 100:0 | 99.6 | 2.2 | 0.0 | 1.1 | 99.6:0.0 |
| 95:5 | 94.8 | 6.2 | 5.2 | 6.2 | 94.8:5.2 |
| 90:10 | 88.9 | 9.1 | 9.7 | 8.5 | 88.9:9.7 |
| 85:15 | 84.7 | 10.2 | 13.7 | 9.4 | 84.7:13.7 |
| 80:20 | 78.9 | 11.5 | 18.7 | 11.0 | 78.9:18.7 |
| 75:25 | 74.3 | 12.0 | 24.2 | 12.0 | 74.3:24.2 |

TABLE 3-continued

Estimated XCI ratio of unphased data by semi-parametric method across 11 in silico experiments.

| Expected XCI ratio | Component 1 mean allelic ration (%) | Standard deviation | Component 2 mean allelic ratio (%) | Standard deviation | Observed XCI ratio |
|---|---|---|---|---|---|
| 70:30 | 69.0 | 12.8 | 27.6 | 12.4 | 69.0:27.6 |
| 65:35 | 64.7 | 12.5 | 32.7 | 12.5 | 64.7:32.7 |
| 60:40 | 58.0 | 13.9 | 37.0 | 13.6 | 58.0:37.0 |
| 55:45 | 51.0 | 14.8 | 49.7 | 14.9 | 51.0:49.7 |
| 50:50 | 48.6 | 14.0 | 47.8 | 14.0 | 48.6:47.8 |

The mean may be biased by the number of SNP markers available and other factors such as variants in genes that normally escape inactivation. However, our simulation shows that when relatively large number of markers are available, both beta testing and SP test can consistently estimate the XCI ratio to the expected (Table 4).

TABLE 4

Number of heterozygous variants to estimate XCI after filtering for coverage.

| Expected XCI | total | ≥10X | ≥20X | ≥30X | ≥40X | ≥50X |
|---|---|---|---|---|---|---|
| 100:0 | 4878 | 3163 | 1606 | 723 | 288 | 119 |
| 95:5 | 4887 | 3203 | 1681 | 756 | 332 | 160 |
| 90:10 | 4882 | 3180 | 1590 | 694 | 308 | 136 |
| 85:15 | 4891 | 3168 | 1598 | 708 | 316 | 138 |
| 80:20 | 4894 | 3203 | 1591 | 693 | 323 | 131 |
| 75:25 | 4887 | 3176 | 1595 | 738 | 310 | 140 |
| 70:30 | 4875 | 3166 | 1627 | 712 | 293 | 137 |
| 65:35 | 4891 | 3165 | 1591 | 686 | 287 | 132 |
| 60:40 | 4878 | 3186 | 1623 | 727 | 313 | 143 |
| 55:45 | 4891 | 3239 | 1695 | 724 | 348 | 151 |
| 50:50 | 4879 | 3205 | 1597 | 703 | 312 | 120 |

Example 3. Clinical Case

A 12 year-old girl of Northern European ancestry presented with a previously undiagnosed, complex neurobehavioral condition manifesting as emotional instability, attention deficit, and delays in development and learning. Prior treatments with medications for poor attention, impulsivity, repetitive behaviors, and learning difficulties started at age 5. She did not have convulsive seizures, but subtle events consisting of staring, loss of awareness, and tremulousness had been observed. MRIs of the brain were normal; EEG showed right posterior temporal sharp waves. The child had an older unaffected brother, and her neurological examination was normal showing concrete ability to respond and interpret questions. Previous CGH array of whole blood from the patient identified a heterozygous deletion between positions 6.4-8.1 Mb on chromosome X. Additionally, HUMARA DNA methylation assay at the AR gene identified 85:15 skewed X inactivation within peripheral blood, providing a hypothesized mechanism for the child's moderate phenotype. To validate previous findings and test our hypothesis, exome and RNAseq sequencing was completed on genomic DNA and total RNA isolated from peripheral blood for the mother, father, daughter trio in order to determine the parent-of-origin of the deletion and resolve whether X inactivation skewing was biased to either the paternal or maternal X chromosome.

Example 4. Exome Analysis

Exome sequencing provided an average of 139 million paired reads with average insert size of 249 base pairs (bp) corresponding to an average 14.8 gigabases (Gb) on the HiSeq2000 platform for the trio. After quality filtering, 121 million reads were aligned to reference genome (NCBI, GRCh37.62) with and average of 88% of reads mapping to. Approximately 97% of target regions had a mean base coverage of 10× (Table 5).

TABLE 5

Summary metrics of Exome Sequencing.

| Exome | Mappable Paired Reads (M) | Mappable Unique Paired Reads (M) | Paired Reads Mapped (M) | Mapped Bases (Gb) | On/Near Target Mapped Bases (Gb) | Mean Coverage Captured Regions (X) | Target Regions Coverage >10X (%) | Fold Enrichment |
|---|---|---|---|---|---|---|---|---|
| Child | 138.58 | 121.30 | 107.22 | 10.79 | 8.13 | 85.71 | 98.05 | 26.17 |
| Mother | 145.77 | 128.17 | 113.15 | 11.39 | 8.54 | 88.79 | 97.73 | 25.71 |
| Father | 133.88 | 115.60 | 101.65 | 10.22 | 7.78 | 84.25 | 97.66 | 26.6 |
| Average | 139.41 | 121.69 | 107.35 | 10.80 | 8.15 | 86.25 | 97.81 | 28.16 |

M = million,

Gb = Gigabases,

X = number of times locus was sequenced

Variant calling identified 85,708 single nucleotide variants (SNPs) and indels in the trio with 85.96% of calls in dbSNP135. Functional evaluation of calls identified 42,192 (46%) missense, 344 non-sense (0.38%), and 48,373 (53%) silent variations. Transition/transversion ratio was 2.31 for all calls, and 2.447 for dbSNP variants. We applied various filtering approaches described elsewhere, but extensive search within Clinvar, The Human Gene Mutation Database, and OMIM did not identify any unambiguous genetic variants that likely caused or contributed to the child's phenotype[3].

Example 5. Characterization and Phasing of Xp22.31 Deletion

Figure 6A:
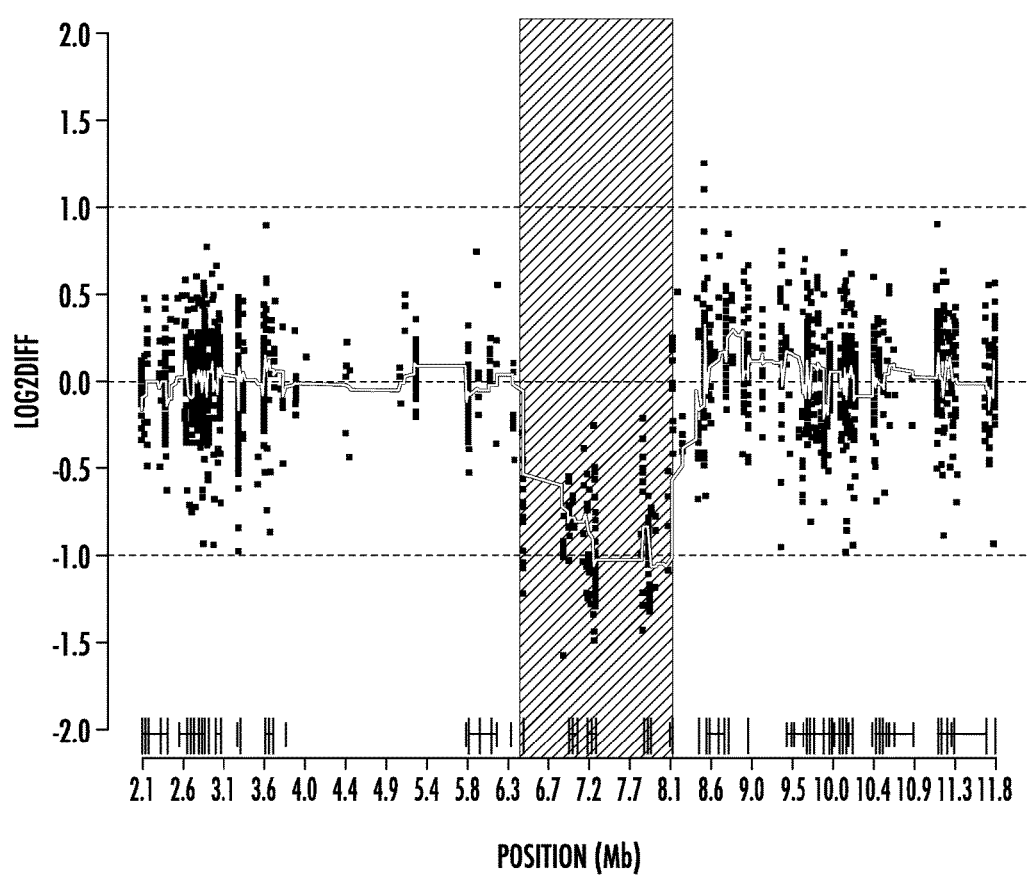
FIGS. 6A-6B show characterization of de novo, interstitial, heterozygous deletion on Xp22.31.
Figure 6B:
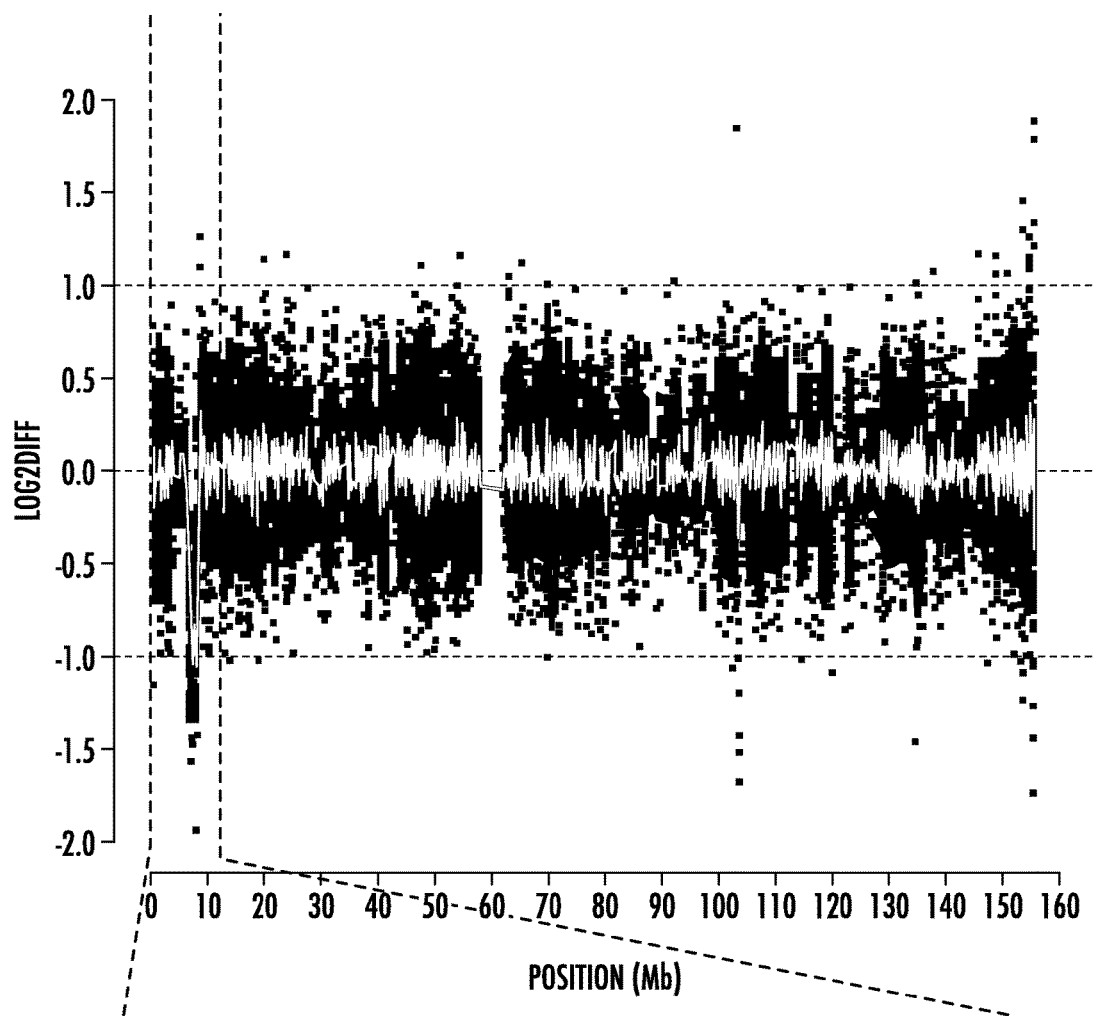

Due to lack of candidate SNP findings from, we used previous information by array CGH to evaluate the chromosome X deletion as potentially disease causing. We compared log 2 normalized physical coverage of the daughter's exome to the log 2 normalized coverage of the mother's (see methods), and observing those regions where the ratio fell below the threshold coverage of −1. Comparative analysis identified the deletion as heterozygous at Xp22.31 with breakpoints at 6,451,600 and 8,095,100, respectively (FIGS. 6A and 6B). Similar comparison to the father's exome indicated that father was hemizygous for this region; therefore the deletion occurred de novo. The distal breakpoint is approximately 50 bp upstream of the variable charged X-linked 3A gene (VCX3A) and the proximal breakpoint resides within the first 100 bp of miR-651 microRNA gene with no known biological function. The deletion encompasses 1,643,501 bp harboring five genes and two microRNA genes (Table 6).

TABLE 6

Genes within 6,4-8,1 Mb interstitial deletion.

| Gene | Gene Name | Start | End | Strand | RefSeq ID | OMIM ID | Phenotype |
|---|---|---|---|---|---|---|---|
| VCX3A | Variably charged X-linked 3A | 6,451,659 | 6,453,159 | − | NM_016379 | 300533 | XLI/MR |
| miR-4787 | microRNA 4787 | 7,065,901 | 7,065,978 | + | NR_039924 | | |
| HDHD1 | Haloaciddehalogenase-like hydrolase domain containing 1 | 6,966,961 | 7,066,231 | − | NM_001135565 | 306480 | escapes XCI |
| STS | Steroid sulfatase, isozyme S | 7,137,472 | 7,272,682 | + | NM_000361 | 300747 | XLI |
| VCX | Variably charged X-linked | 7,810,303 | 7,812,184 | + | NM_013452 | 300229 | |
| PNPLA4 | Patatin-like phospholipase domain containing 4 | 7,866,804 | 7,895,475 | − | NM_004860 | 300102 | |
| miR-651 | microRNA 651 | 8,095,0068 | 6,095,102 | + | NR_030380 | | |

Figure 7:
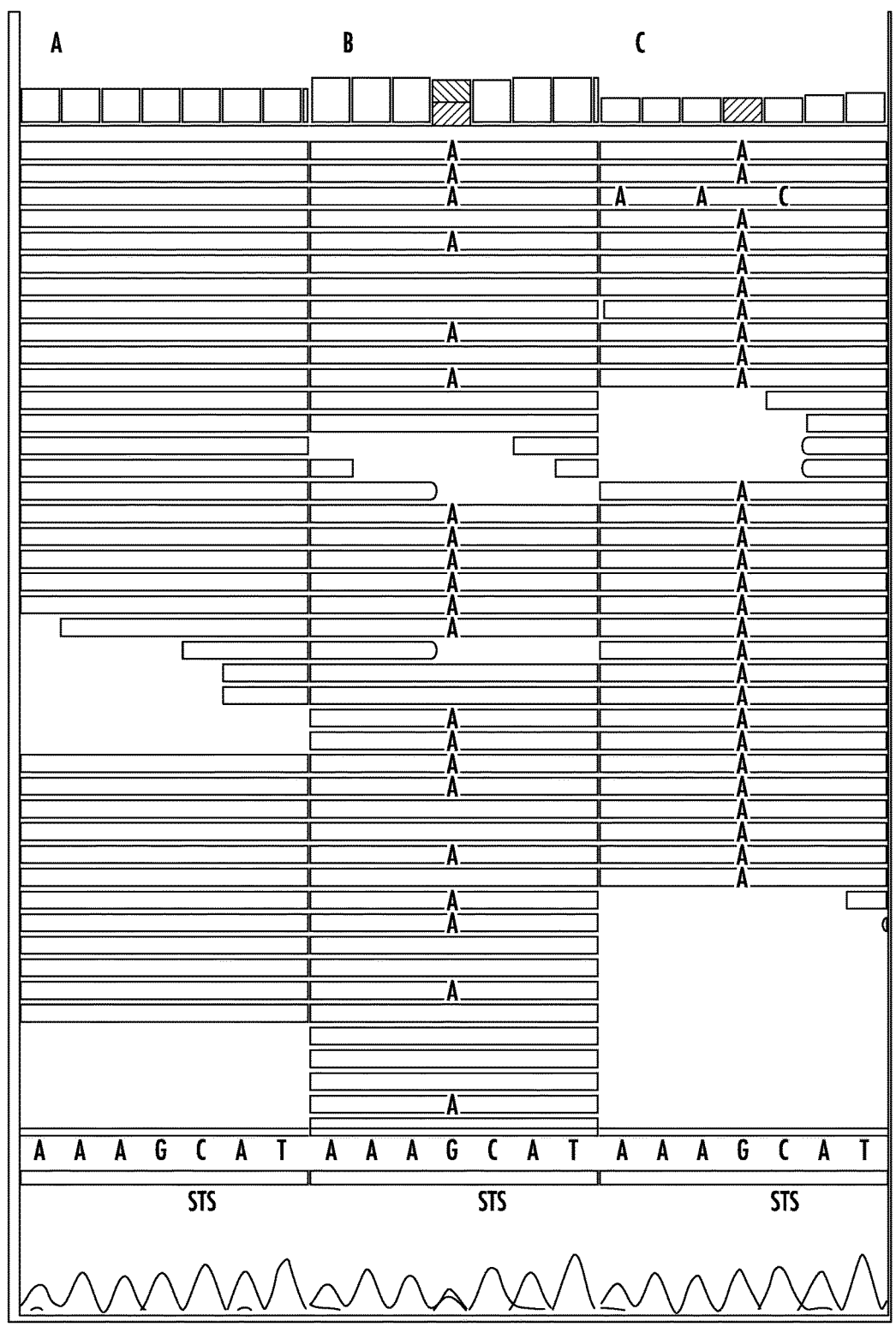
FIG. 7 shows determination of out-of-phase of rs5933863. Next-generation sequencing traces visualized using the Integrated Genomic Viewer (IGV) and below them the corresponding Sanger traces of rs5933863 G>A alleles in the STS gene that helped determine phase and origin of the 1.7 Mb deletion on chromosome X [51]. Our patient's (a) IGV and Sanger traces indicate that she is either homozygous G/G or hemizygous "G" genotype at this position. The mother's (b) and the father's (c) traces indicate that they are "G/A" and "A" genotype, respectively.

This region was in concordance with the array CGH. The deletion was phased to the paternally inherited chromosome based on rs5933863, at X:7,270,694 G>A in the 3' untranslated UTR region of the STS gene (NM_000351) (FIG. 7). The affected child's genotype was homozygous G/G, the mother's was heterozygous G/A, and the father's was homozygous alternative A/A. Recoding based on anticipated ploidy, the child's genotype is "G", the mother remains "G/A", and the father with a single X chromosome is recoded "A". Principles of X-linked inheritance dictate that the child must have a heterozygous genotype G/A at this position. Since she is missing the paternal allele A and has an apparent genotype of "G", there is evidence that the region containing this SNP on the paternal X chromosome was deleted resulting in an out-of-phase genotype. This out-of-phase coding SNP was validated by Sanger method in the trio.

Example 6. Estimation of XCI Ratio from RNAseq Experiment

RNAseq was conducted on mRNA obtained from peripheral blood. Sequencing resulted in an average of 116 million paired reads per sample mapping to GRCh37.62 human reference genome (Table 7).

TABLE 7

Summary metrics of RNA Sequencing.

| RNAseq | Quality Reads Mapped (M) | Reads Mapped in Pairs (M) | Reads Mapped in pairs (%) | Mappable Bases (Gb) | Mapped Bases (Gb) | FPKM >1.0 #genes/total annotated genes on X | Median Insert Size |
|---|---|---|---|---|---|---|---|
| Child | 95.44 | 84.13 | 88.15 | 8.05 | 8.05 | 346/2688 | 154 |
| Mother | 154.90 | 135.39 | 87.41 | 13.54 | 13.54 | 374/2688 | 156 |

TABLE 7-continued

Summary metrics of RNA Sequencing.

| RNAseq | Quality Reads Mapped (M) | Reads Mapped in Pairs (M) | Reads Mapped in pairs (%) | Mappable Bases (Gb) | Mapped Bases (Gb) | FPKM >1.0 #genes/total annotated genes on X | Median Insert Size |
|---|---|---|---|---|---|---|---|
| Father | 99.18 | 83.11 | 83.80 | 8.89 | 8.90 | 362/2688 | 154 |
| Average | 116.51 | 100.88 | 86.58 | 10.16 | 10.16 | 361/2688 | 155 |

M = million,
Gb = Gigabases,
genes = based on Cuffdiff output of ensemble version 63 annotation and found in genes.fpkm_tracking.txt file for each individual.

Figure 8:
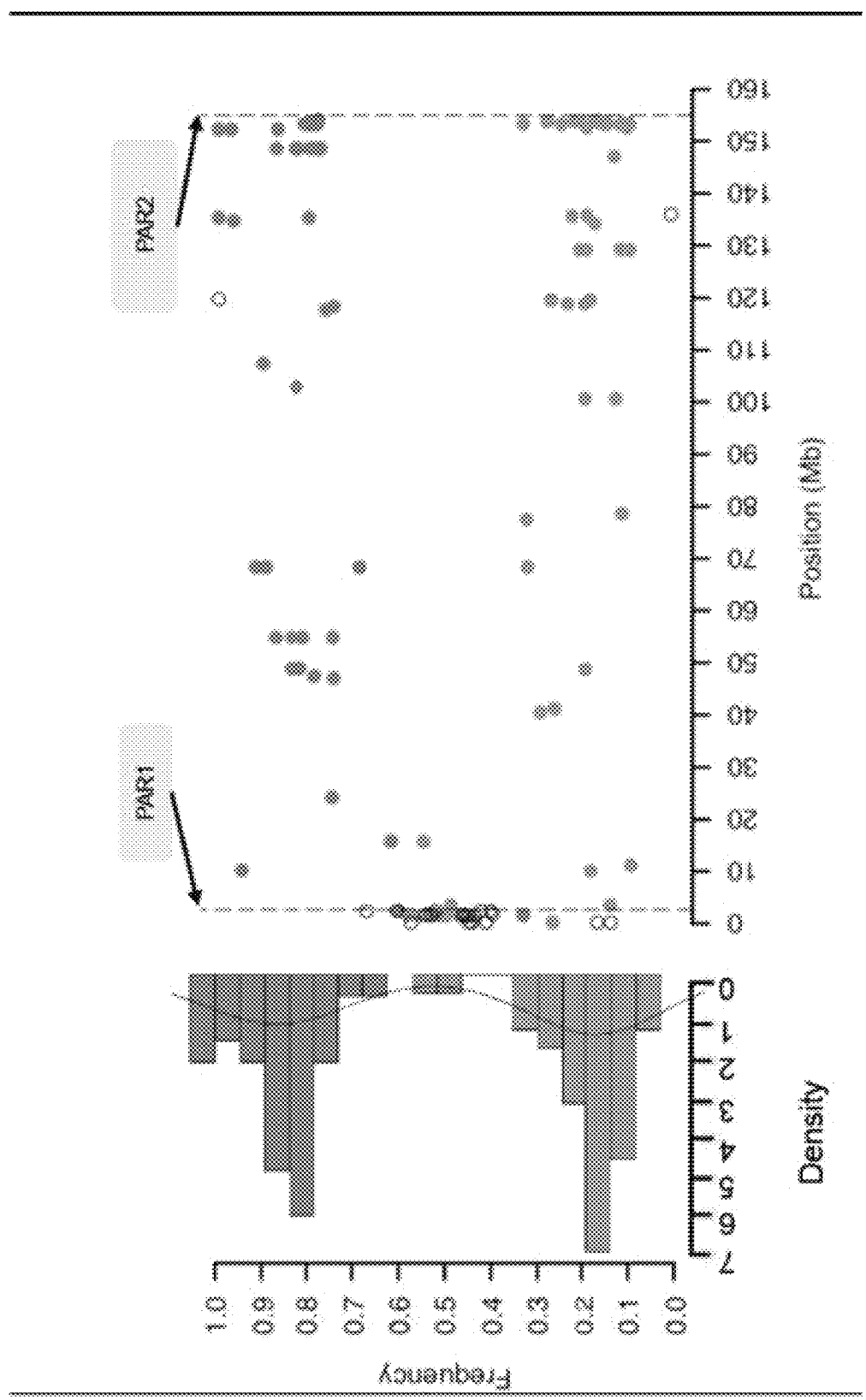
FIG. 8 shows phased allelic expression on chromosome X. Allelic ratio of heterozygous SNPs show bimodal distribution which corresponds to a maternal (magenta) and paternal (green) distributions after phasing of X-linked alleles. Essentially all high quality heterozygous SNPs could be phased based on transmission of alleles with the X-linked region. Unphased SNPs (clear circle) lie predominantly in the pseudo-autosomal region (PAR1) except two hits with X-linked region. The scatter plot indicates that biased expression in favor of the maternally inherited alleles is preserved across the entire length of the chromosome. Each allele is covered by at least 20 reads.

From the, exome variant call set 1,729 single nucleotide variants including indels mapped to chromosome X, of which 901 were called heterozygous in the affected child. 374 calls were heterozygous SNPs within transcripts, and 325 were X-linked, outside pseudoatosomal PAR1 and PAR2 regions[25]. 226 variants were high quality with score PASS by GATK Variant Recalibration. Next we selected variants that were previously documented in dbSNP build 135. A total of 83 SNPs were covered with at least 20 reads. 37 phased to the maternal X and 44 to the paternal X, and two Mendelian errors. The 37 maternally inherited alleles were from 23 genes, with 19 genes with a single heterozygous expressed variant and 4 with more than two heterozygous expressed variants. The 44 paternal variant alleles were from 31 genes, and 22 of them had a single heterozygous variant expressed and 9 had more than one heterozygous variants. The allele ratio distribution indicated bimodal distribution showing lower expression of paternally inherited heterozygous SNPs (FIG. 8). The XCI ratio estimated from phased alleles was 82.7:20.3 and from the unphased allelic data was 82.2:19.2 consistent with moderately skewed X inactivation and with 85:15 ratio obtained by the HUMARA methylation assay.

The integration of phase information had minimal effect to final estimate indicating the power of the semi-parametric model. In addition to the clinical case we estimated XCI ratio in 4 additional female individuals from our clinical sequencing center (FIGS. 9A-9E). In each case XCI was estimated by our RNAseq approach and the HUMARA assay. A single case was uninformative for the HUMARA, which can be due to homozygosity at the methylation sensitive repeat sequence of the AR locus (FIG. 9E). In 3 out of the 5 cases (60%), the HUMARA method suggested moderately skewed XCI ratio (>80:20) (FIGS. 9A, 9C, and 9D). However, expression analysis supported strong correlation between the three methods only in the clinical case of this report where skewed XCI was estimated by all three methods (FIG. 9A). In two of the remaining four cases skewed XCI was not supported by the RNAseq analysis (FIGS. 9C and 9D). In a single case all three methods predicted random XCI ratio (FIG. 9B). In general the Beta and the Semi-Parametric methods have a high correlation with each other (Pearson's r=0.99), but these approaches have weaker correlation with HUMARA (SP Pearson's r=0.84, Beta Pearson's r=0.80). In general, we see a lower XCI ratio estimated by allele expression analysis than by HUMARA. Estimates of XCI ratio may be biased by reference bias in read mapping, insufficient coverage at heterozygous loci, and by heterogeneous gene expression due to methylation and cis-acting regulatory mechanisms.

Example 7. Identification of Genes that Escape X Inactivation

Phased, allele-specific expression analysis highlighted a number of variants in genes that may escape inactivation. Escape of X inactivation results in bi-allelic expression of genes from both the active X and the inactive X in the same cell and can contribute to phenotypic variability in females who are carriers of X-linked disease.[36]. Therefore a catalogue of escape genes in clinical evaluation may contribute to our better understanding of clinical symptoms and may offer treatment options. We identified escape genes by examining 325 heterozygous loci across X and the deviation of their allelic ratio from the mean allelic ratio of each phased distribution. We defined a candidate escape gene by having a heterozygous SNP loci with an allelic ratio that is two standard deviations outside the mean allelic ratio of the chromosome-wide allelic distribution and showing bi-allelic expression. Bi-allelic expression was defined as allelic ratio between 0.1 and 0.9. Therefore if a paternally inherited variant had an allelic ratio of 0.49 and the mean allele ratio of the chromosome-wide paternal alleles was 0.203 with a standard deviation of 0.09, that variant was outside 2 standard deviation of the mean, and it was bi-allelic expressed. Of the 325 X-linked heterozygous alleles 15 showed bi-allelic expression in 12 genes, but 7 was considered as false positive due to low read coverage (<7X)(Table 8)[37].

TABLE 8

Escape of X inactivation status of candidate variants identified in the patient.

| Position | dbSNP | Variant phase | Allelic ratio | Read depth | Gene | Zhang et al. |
|---|---|---|---|---|---|---|
| X: 3,524,309 | rs6567569 | paternal | 0.49 | 55 | PRKX | Escape |
| X: 10,203,342 | rs41305355 | maternal | 0.38 | 8 | CLCN4 | Heterogeneous |
| X: 10,204,267 | rs4830442 | maternal | 0.50 | 12 | CLCN4 | Heterogeneous |
| X: 15,339,588 | rs148660178 | maternal | 0.50 | 2 | PIGA | Inactive |
| X: 15,801,330 | rs12841514 | paternal | 0.55 | 20 | CA5B | Heterogeneous |
| X: 15,801,643 | rs28707735 | paternal | 0.56 | 9 | CA5B | Heterogeneous |
| X: 15,802,800 | rs5980189 | paternal | 0.50 | 4 | CA5B | Heterogeneous |
| X: 20,143,370 | rs13179 | paternal | 0.50 | 10 | EIF1AX | Escape |
| X: 41,374,523 | rs5918192 | paternal | 0.60 | 5 | CASK | Inactive |

TABLE 8-continued

Escape of X inactivation status of candidate variants identified in the patient.

| Position | dbSNP | Variant phase | Allelic ratio | Read depth | Gene | Zhang et al. |
|---|---|---|---|---|---|---|
| X: 46,358,046 | rs148701104 | paternal | 0.50 | 2 | ZNF673 | Inactive |
| X: 48,690,749 | rs11538178 | paternal | 0.47 | 15 | PCSK1N | Inactive |
| X: 100,881,434 | rs6995 | paternal | 0.50 | 4 | ARMCX3 | Heterogeneous |
| X: 132,438,872 | rs1129980 | paternal | 0.50 | 2 | GPC4 | Heterogeneous |
| X: 153,694,334 | rs5945430 | paternal | 0.50 | 8 | PLXNA3 | Heterogeneous |
| X: 153,759,858 | rs1050757 | paternal | 0.67 | 3 | G6PD | Heterogeneous |

As shown in Table 8, these 15 variants were found to escape inactivation due to their allelic ratio fell outside 2 standard deviation of the man allelic frequency of the phased allelic distributions. Also included are the chromosomal location, the dbSNP135 identifiers, phase of the variant allele, the observed allelic ratio, the read depth, and the observed escape status in multiple individuals assessed by Zhang et al. and listed under the header Zhang et al.

From the remaining 8 variants, all but one (PCSK1N) was consistent with both hybrid cell line and lymphoblast data showing full or partial consistency[36, 37]. PCSK1N is a Protein Convertase 1 Inhibitor that has not been associated with escape of X inactivation. PCSK1N and associated propeptide may have a role in body weight and behavior in mice, but its dosage affect due to XCI remain to be elucidated [38]. The distribution of the 8 escape genes across the X chromosome was consistent with the regions that contain the highest density of escape genes, and were mostly located on the short arm of chromosome X [39].

Example 8: Discussion

In this study we applied integrated whole-exome and mRNA sequencing to simultaneously evaluate the functional effect of coding variations in the process of clinical diagnosis. Although previous clinical testing suggested a mechanism for her disease, with the combined analysis of the trio exome and the patient's mRNA expression that we are now able to hypothesize a mechanism for her phenotype. Variant filtration approaches after trio exome sequencing did not result in the identification of strong candidate causal variations. Although there was suggestive evidence from the patient's array CGH that the disease pathology may be related to a heterozygous deletion on Xp22.31 only incorporation of SNP phasing and comparative analysis of sequenced reads that we were able to determine that the deletion occurred de novo. Genes associated with neurological dysfunction including a number of variable-charge X-linked genes lie within the deletion (VCX, VCX3A)[40].

Although we were not able to detect lymphocyte expression of any of the VCX genes, there is suggestive evidence these genes have roles in cognitive function. VCX3A overexpression in rat hippocampal neurons increase neurite outgrowth that may positively influence synaptic plasticity [40]. Furthermore, some males who are hemizygous for a recurrent Xp22.31 deletion and have X-linked ichthyosis (OMIM 308100) also demonstrate mental retardation [41]. This region appears to be a hotspot for copy number changes, complex duplications, and triplications, suggesting that the instability of this region may contribute to disease risk [42]. The inherent limitation of our approach is that our resolution to define the exact genomic content of the deletion is reduced by exome sequencing and can only be circumvented with whole-genome sequencing approaches. However, whole genomic approaches in family studies are still uneconomical.

Phased and unphased allele-specific expression in the patient was concordant with the HUMARA assay and indicated moderately skewed XCI. The contribution of skewed XCI to her condition is not clear, although the phased XCI ratio allows us to develop hypothesis about the molecular mechanism that underlie her condition. Random XCI in this patient and the dominant negative affect of the deletion would suggest a more sever neurological condition. However, females who are carriers for deleterious chromosomal mutations may not present clinical symptoms due to selective advantage and preferential expression of the normal X[16, 43]. These females are usually heterozygous for an X-linked deleterious allele and have skewed XCI. The patient has skewed XCI and is heterozygous for the deletion but showing some mild neurological condition, suggesting that the preferential expression of the cytogenetically normal X may be compensating for the deleterious effect of the deletion. While insufficient cases have been reported to provide statistical significance, females who were diagnosed with Xp22.31 microduplication and preferentially silenced the X with the microduplication had normal phenotype while those who preferentially express the X with the microduplication had intellectual disability (ID) [44]. It is plausible that loss of a chromosome copy at Xp22.31 has different clinical manifestation than copy gain. Therefore the contribution of Xp22.31 rearrangements to neurological dysfunction need further study. For the patient sequenced in this study, our data are consistent with a model that the preferential expression of the cytogenetically normal maternal X chromosome may have contributed to her mild cognitive phenotype. While different tissues may exhibit different levels of XCI, there is significant correlation between XCI pattern obtained from blood and cerebrum [45]. If the results obtained from sequencing of the whole blood are applicable to the brain, it is possible that the effect of those cells that express the paternal X may contribute to her symptoms. Our ability to uncover molecular mechanisms by DNA and RNA sequencing in patient's surrogate tissue (peripheral blood) that may correlate with phenotype in the central nervous system argues for potential benefit in clinical diagnostic cases that remain unresolved. This is supported by a number of studies that find a strong correlation in gene expression profile in blood with affected status in such diseases as Parkinson's Disease and Huntington's Disease [46, 47]

Our simulation proposed an approach to estimate XCI ratio using chromosome-wide SNP expression and found that phased and unphased SNPs can equally estimate the ratio with both beta and semi-parametric model. Even if research and clinical sequencing application will be limited in sequence coverage, our method is able to predict XCI at high concordance with expected as low as 10× coverage. Our method also allowed for base error rate therefore providing a more realistic sequence data. Our approach based on read count, and relative ratio estimation of variant alleles, can be applied to other sequencing platforms and to other expressed regions of the genome that are targeted by RNAseq. Principles of skewed expression demonstrated in this study could be relevant to imprinted portions of autosomes and therefore applicable to disorders like Prader-Willi and Angelman syndromes [48]. Skewed expression of autosomal heterozygous alleles can be markers for imprinted regions, and may uncover cis-regulatory elements.

Experimental data suggests that RNAseq not always concordant with standard methylation assay. Although our samples size was small, and two samples showed concordance with HUMARA prediction, RNAseq may better estimate the true activity of the chromosome copies. HUMARA assay targets a single genomic locus and relies on the methylation of a repeat of the sequence that is targeted by methylation sensitive restriction enzyme. Deletions, copy number changes, homozygosity at the AR locus, biases due to enzymatic and PCR inefficiency, hypo-methylation of restriction enzyme target, difficulties associated with data interpretation, and the challenges associated with the amplification of repeat regions may influence assay results.[20].

Our approach is dependent on the accuracy and sensitivity of multiple SNP markers expressed in the X-linked region. There is heterogeneity how the expression of X-linked genes are regulated by epigenetic mechanisms, sampling alleles from genes with various expression to infer X inactivation ratio may be inconsistent with other methods but provides an accurate picture of the molecular characteristics of the tissue source[36]. We did not exclude escape or methylated genes from our analysis that may have contributed to an overall lower ratio than methylation assay. Methylation based assessment may not be concordant with expression based methods due to differences in the technology and applied analytical methods. RNAseq is also prone to technical and analytical variability that may affect XCI ratio therefore transcription-based validation assays are useful to improve our approach[36, 49, 50]. The use of direct expression analysis of multiple SNP markers may also increase our power to accurately estimate XCI, providing a basis to improve our definition of clinically significant XCI ratio boundaries. However a more systematic screening of XCI by RNA-sequencing across a series of X-linked disorders in females may greatly enhance our understanding of the underlying cause of phenotypic variability.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference herein in their entirety for all purposes.

The publications discussed herein are provided solely for their disclosure prior to the filing date of the present application. Nothing herein is to be construed as an admission that the present invention is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

REFERENCES

1. Dixon-Salazar T J, Silhavy J L, Udpa N, Schroth J, Bielas S, Schaffer A E, Olvera J, Bafna V, Zaki M S, Abdel-Salam G H, Mansour L A, Selim L, Abdel-Hadi S, Marzouki N, Ben-Omran T, Al-Saana N A, Sonmez F M, Celep F, Azam M, Hill K J, Collazo A, Fenstermaker A G, Novarino G, Akizu N, Garimella K V, Sougnez C, Russ C, Gabriel S B, Gleeson J G: Exome Sequencing Can Improve Diagnosis and Alter Patient Management. *Science Translational Medicine* 2012, 4: 138ra78-138ra78.
2. Yang Y, Muzny D M, Reid J G, Bainbridge M N, Willis A, Ward P A, Braxton A, Beuten J, Xia F, Niu Z, Hardison M, Person R, Bekheirnia M R, Leduc M S, Kirby A, Pham P, Scull J, Wang M, Ding Y, Plon S E, Lupski J R, Beaudet A L, Gibbs R A, Eng CM: Clinical Whole-Exome Sequencing for the Diagnosis of Mendelian Disorders. *N Engl J Med* 2013:131002140031007.
3. Gilissen C, Hoischen A, Brunner H G, Veltman J A: Disease gene identification strategies for exome sequencing. *Eur J Hum Gen* 2012, 20:490-497.
4. Wang Z, Gerstein M, Snyder M: RNA-Seq: a revolutionary tool for transcriptomics. *Nat Rev Genet* 2009, 10:57-63.
5. Shah S P, Roth A, Goya R, Oloumi A, Ha G, Zhao Y, Turashvili G, Ding J, Tse K, Haffari G, Bashashati A, Prentice L M, Khattra J, Burleigh A, Yap D, Bernard V, McPherson A, Shumansky K, Crisan A, Giuliany R, Heravi-Moussavi A, Rosner J, Lai D, Birol I, Varhol R, Tam A, Dhalla N, Zeng T, Ma K, Chan S K, et al.: The clonal and mutational evolution spectrum of primary triple-negative breast cancers. *Nature* 2012, 486: 395-399.
6. Craig D W, O'Shaughnessy J A, Kiefer J A, Aldrich J, Sinari S, Moses $T_M$, Wong S, Dinh J, Christoforides A, Blum J L, Aitelli C L, Osborne C R, Izatt T, Kurdoglu A, Baker A, Koeman J, Barbacioru C, Sakarya O, La Vega De F M, Siddiqui A, Hoang L, Billings P R, Salhia B, Tolcher A W, Trent J M, Mousses S, Hoff Von D, Carpten J D: Genome and Transcriptome Sequencing in Prospective Metastatic Triple-Negative Breast Cancer Uncovers Therapeutic Vulnerabilities. *Molecular Cancer Therapeutics* 2013, 12:104-116.
7. Liang W S, Craig D W, Carpten J, Borad M J, Demeure M J, Weiss G J, Izatt T, Sinari S, Christoforides A, Aldrich J, Kurdoglu A, Barrett M, Phillips L, Benson H, Tembe W, Braggio E, Kiefer J A, Legendre C, Posner R, Hostetter G H, Baker A, Egan J B, Han H, Lake D, Stites E C, Ramanathan R K, Fonseca R, Stewart A K, Hoff Von D: Genome-Wide Characterization of Pancreatic Adenocarcinoma Patients Using Next Generation Sequencing. *PLoS ONE* 2012, 7:e43192.
8. Babak T, DeVeale B, Armour C, Raymond C, Cleary M A, van der Kooy D, Johnson J M, Lim L P: Global Survey of Genomic Imprinting by Transcriptome Sequencing. *Current Biology* 2008, 18:1735-1741.
9. Wang X, Sun Q, McGrath S D, Mardis E R, Soloway P D, Clark A G: Transcriptome-Wide Identification of Novel Imprinted Genes in Neonatal Mouse Brain. *PLoS ONE* 2008, 3:e3839.

10. Lyon M F: Gene Action in the X-chromosome of the Mouse. *Nature* 1961, 4773:372-373.
11. Muller H J: Further studies on the nature and causes of gene mutations. *Int. Congress of Genetics* 1932, 1:3-255.
12. Augui S, Nora E P, Heard E: Regulation of X-chromosome inactivation by the X-inactivation centre. *Nature Publishing Group* 2011, 12:429-442.
13. Amos-Landgraf J M, Cottle A, Plenge R M, Friez M, Schwartz C E, Longshore J, Willard H F: X Chromosome—Inactivation Patterns of 1,005 Phenotypically Unaffected Females. *Am J Hum Genet* 2006, 79:493-499.
14. Migeon B R: The role of X inactivation and cellular mosaicism in women's health and sex-specific diseases. *JAMA: the journal of the American Medical Association* 2006, 295:1428-1433.
15. Ørstavik KH: X chromosome inactivation in clinical practice. *Hum Genet* 2009, 126:363-373.
16. Plenge R M, Stevenson R A, Lubs H A, Schwartz C E, Willard H F: Skewed X-chromosome inactivation is a common feature of X-linked mental retardation disorders. *Am J Hum Genet* 2002, 71:168-173.
17. Van Esch H, Bauters M, Ignatius J, Jansen M, Raynaud M, Hollanders K, Lugtenberg D, Bienvenu T, Jensen L R, Gecz J, Moraine C, Marynen P, Fryns Froyen G: Duplication of the MECP2 region is a frequent cause of severe mental retardation and progressive neurological symptoms in males. *Am J Hum Genet* 2005, 77:442-453.
18. Allen R C, Zoghbi H Y, Moseley A B, Rosenblatt H M, Belmont J W: Methylation of Hpall and HhaI sites near the polymorphic CAG repeat in the human androgen-receptor gene correlates with X chromosome inactivation. *Am J Hum Genet* 1992, 51:1229-1239.
19. Busque L, Paquette Y, Provost S, Roy D C, Levine R L, Mollica L, Gary Gilliland D: Skewing of X-inactivation ratios in blood cells of aging women is confirmed by independent methodologies. *Blood* 2009, 113:3472-3474.
20. Swierczek S I, Piterkova L, Jelinek J, Agarwal N, Hammoud S, Wilson A, Hickman K, Parker C J, Cairns B R, Prchal J T: Methylation of AR locus does not always reflect X chromosome inactivation state. *Blood* 2012, 119:e100-e109.
21. Kim D, Pertea G, Trapnell C, Pimentel H, Kelley R, Salzberg S L: TopHat2: accurate alignment of transcriptomes in the presence of insertions, deletions and gene-fusions. *Genome Biology* 2013, 14:R36.
22. Rozowsky J, Abyzov A, Wang J, Alves P, Raha D, Harmanci A, Leng J, Bjornson R, Kong Y, Kitabayashi N, Bhardwaj N, Rubin M, Snyder M, Gerstein M: AlleleSeq: analysis of allele-specific expression and binding in a network framework. *Molecular Systems Biology* 2011, 7:1-15.
23. Stevenson K R, Coolon J D, Wittkopp P J: Sources of bias in measures of allele-specific expression derived from RNA-seq data aligned to a single reference genome. *BMC Genomics* 2013, 14:1-1.
24. Li H, Handsaker B, Wysoker A, Fennell T, Ruan J, Homer N, Marth G, Abecasis G, Durbin R, 1000 Genome Project Data Processing Subgroup: The Sequence Alignment/Map format and SAMtools. *Bioinformatics* 2009, 25:2078-2079.
25. Mangs A H, Morris B J: The human pseudoautosomal region (PAR): origin, function and future. *Current genomics* 2007, 8:129.
26. McKenna A, Hanna M, Banks E, Sivachenko A, Cibulskis K, Kernytsky A, Garimella K, Altshuler D, Gabriel S, Daly M, DePristo M A: The Genome Analysis Toolkit: A MapReduce framework for analyzing next-generation DNA sequencing data. *Genome Research* 2010, 20:1297-1303.
27. Skelly D A, Johansson M, Madeoy J, Wakefield J, Akey J M: A powerful and flexible statistical framework for testing hypotheses of allele-specific gene expression from RNA-seq data. *Genome Research* 2011, 21:1728-1737.
28. Zhou Y H, Xia K, Wright F A: A powerful and flexible approach to the analysis of RNA sequence count data. *Bioinformatics* 2011, 27:2672-2678.
29. Hardcastle T J, Kelly K A: Empirical Bayesian analysis of paired high-throughput sequencing data with a beta-binomial distribution. *BMC Bioinformatics* 2013, 14:135.
30. Sun W: A Statistical Framework for eQTL Mapping Using RNA-seq Data. *Biometrics* 2011, 68:1-11.
31. Hunter D R, Wang S, Hettmansperger T P: Inference for mixtures of symmetric distributions. *Ann Statist* 2007, 35:224-251.
32. Bordes L, Chauveau D, Vandekerkhove P: A stochastic EM algorithm for a semiparametric mixture model. *Computational Statistics & Data Analysis* 2007, 51:5429-5443.
33. Li H, Durbin R: Fast and accurate short read alignment with Burrows-Wheeler transform. *Bioinformatics* 2009, 25:1754-1760.
34. DePristo M A, Banks E, Poplin R, Garimella K V, Maguire J R, Hartl C, Philippakis A A, del Angel G, Rivas M A, Hanna M, McKenna A, Fennell T J, Kernytsky A M, Sivachenko A Y, Cibulskis K, Gabriel S B, Altshuler D, Daly M J: A framework for variation discovery and genotyping using next-generation DNA sequencing data. *Nature Publishing Group* 2011, 43:491-498.
35. Trapnell C, Williams B A, Pertea G, Mortazavi A, Kwan G, van Baren M J, Salzberg S L, Wold B J, Pachter L: Transcript assembly and quantification by RNA-Seq reveals unannotated transcripts and isoform switching during cell differentiation. *Nature Biotechnology* 2010, 28:511-515.
36. Carrel L, Willard H F: X-inactivation profile reveals extensive variability in X-linked gene expression in females. *Nature* 2005, 434:400-404.
37. Zhang Y, Castillo-Morales A, Jiang M, Zhu Y, Hu L, Urrutia A O, Kong X, Hurst L D: Genes That Escape X-Inactivation in Humans Have High Intraspecific Variability in Expression, Are Associated with Mental Impairment but Are Not Slow Evolving. *Molecular Biology and Evolution* 2013.
38. Morgan D J, Wei S, Gomes I, Czyzyk T, Mzhavia N, Pan H, Devi L A, Fricker L D, Pintar J E: The propeptide precursor proSAAS is involved in fetal neuropeptide processing and body weight regulation. *Journal of Neurochemistry* 2010.
39. Disteche C M: Escapees on the X chromosome. *Proc Natl Acad Sci USA* 1999, 96:14180-14182.
40. Jiao X, Chen H, Chen J, Herrup K, Firestein B L, Kiledjian M: Modulation of Neuritogenesis by a Protein Implicated in X-Linked Mental Retardation. *Journal of Neuroscience* 2009, 29:12419-12427.
41. Van Esch H: Deletion of VCX-A due to NAHR plays a major role in the occurrence of mental retardation in patients with X-linked ichthyosis. *Human Molecular Genetics* 2005, 14:1795-1803.
42. Liu P, Erez A, Sreenath Nagamani S C, Bi W, Carvalho C M B, Simmons A D, Wiszniewska J, Fang P, Eng P A, Cooper M L, Sutton V R, Roeder E R, Bodensteiner J B, Delgado M R, Prakash S K, Belmont J W, Stankiewicz P, Berg J S, Shinawi M, Patel A, Cheung S W, Lupski J R:

Copy number gain at Xp22.31 includes complex duplication rearrangements and recurrent triplications. *Human Molecular Genetics* 2011, 20:1975-1988.
43. Desai V, Donsante A, Swoboda K J, Martensen M, Thompson J, Kaler S G: Favorably skewed X-inactivation accounts for neurological sparing in female carriers of Menkes disease. *Clinical Genetics* 2011, 79:176-182.
44. Li F, Shen Y, Köhler U, Sharkey F H, Menon D, Coulleaux L, Malan V, Rio M, McMullan D J, Cox H, Fagan K A, Gaunt L, Metcalfe K, Heinrich U, Hislop G, Maye U, Sutcliffe M, Wu B-L, Thiel B D, Mulchandani S, Conlin L K, Spinner N B, Murphy K M, Batista D A S: Interstitial microduplication of Xp22.31: Causative of intellectual disability or benign copy number variant? *European Journal of Medical Genetics* 2010, 53:93-99.
45. Bittel D C, Theodoro M F, Kibiryeva N, Fischer W, Talebizadeh Z, Butler M G: Comparison of X-chromosome inactivation patterns in multiple tissues from human females. *Journal of Medical Genetics* 2008, 45:309-313.
46. Scherzer C R, Eklund A C, Morse L J, Liao Z, Locascio J J, Fefer D, Schwarzschild M A, Schlossmacher M G, Hauser M A, Vance J M, Sudarsky L R, Standaert D G, Growdon J H, Jensen R V, Gullans S R: Molecular markers of early Parkinson's disease based on gene expression in blood. *Proc Natl Acad Sci USA* 2007, 104:955-960.
47. Borovecki F, Lovrecic L, Zhou J, Jeong H, Then F, Rosas H D, Hersch S M, Hogarth P, Bouzou B, Jensen R V: Genome-wide expression profiling of human blood reveals biomarkers for Huntington's disease. *Proc Natl Acad Sci USA* 2005, 102:11023-11028.
48. Biliya S, Bulla L A: Genomic imprinting: the influence of differential methylation in the two sexes. *Experimental Biology and Medicine* 2010, 235:139-147.
49. Moreira de Mello J C, Araújo É S S de, Stabellini R, Fraga A M, Souza J E S de, Sumita D R, Camargo A A, Pereira L V: Random X Inactivation and Extensive Mosaicism in Human Placenta Revealed by Analysis of Allele-Specific Gene Expression along the X Chromosome. *PLoS ONE* 2010, 5:e10947.
50. Swierczek S I, Agarwal N, Nussenzveig R H, Rothstein G, Wilson A, Artz A, Prchal J T: Hematopoiesis is not clonal in healthy elderly women. *Blood* 2008, 112:3186-3193.
51. Robinson J T, Thorvaldsdottir H, Winckler W, Guttman M, Lander E S, Getz G, Mesirov J P: Integrative genomics viewer. *Nature Biotechnology* 2011, 29:24-26.

What is claimed is:

1. A process of characterizing X chromosome inactivation (XCI) in a female subject, the process comprising:
   (a) obtaining a first biological sample comprising nucleic acids from the female subject, a second biological sample comprising nucleic acids from the biological mother of the female subject, and a third biological sample comprising nucleic acids from the biological father of the female subject;
   (b) isolating the nucleic acids from the first biological sample, the second biological sample, and the third biological sample;
   (c) performing whole genome sequencing or whole exome sequencing by next generation sequencing of the isolated nucleic acids from the second biological sample, and the third biological sample;
   (d) identifying from the whole genome sequencing or whole exome sequencing a plurality of X-linked variant alleles, wherein the female subject is heterozygous for the X-linked variant alleles;
   (e) performing whole transcriptome sequencing by next generation sequencing of the isolated nucleic acids from the first biological sample;
   (f) measuring from the whole transcriptome sequencing allelic ratios of the X-linked variant alleles at each heterozygous locus; and (g) characterizing an XCI ratio in the female subject by determining a combined mean allelic ratio for the X-linked variant alleles from the allelic ratios at each heterozygous locus.

2. The process of claim 1, further comprising performing whole genome sequencing or whole exome sequencing by next generation sequencing of the isolated nucleic acids from the first biological sample.

3. The process of claim 1, wherein the whole transcriptome sequencing is performed simultaneously with step (c) and comprises whole mRNA sequencing.

4. The process of claim 1, wherein the isolated nucleic acids in step (c) comprises genomic DNA and the isolated nucleic acids in step (e) comprise total RNA or mRNA.

5. A process of identifying an X-linked disorder in a female subject, the process comprising:
(a) characterizing X chromosome inactivation (XCI) in the female subject according to the process of claim 1; and
(b) identifying an X-linked disorder in the female subject if the combined mean allelic ratio for the X-linked variant alleles is substantially skewed, wherein the combined mean allelic ratio is substantially skewed if expression of the X-linked variant alleles from the biological mother of the female subject compared to expression of the X-linked variant alleles from the biological father of the female subject differs by at least a ratio of 65:35.

6. The process of claim 5, wherein the expression of at least one of the X-linked variant alleles differs by at least 80:20.

7. The process of claim 5, wherein the X-linked disorder is at least partially caused by a change in mode and magnitude of XCI.

8. The process of claim 7, wherein the mode of XCI is determined by phasing of the chromosome-wide X-linked heterozygous SNP alleles of the female subject.

9. The process of claim 7, wherein the magnitude of XCI is determined in silico by computer simulation of phased or unphased chromosome-wide X-linked heterozygous SNP alleles of the female subject or the magnitude of XCI is determined by allele-specific expression analysis of phased or unphased chromosome-wide X-linked heterozygous SNP alleles of the female subject that are transcribed into mRNA.

10. The process of claim 9, wherein the XCI ratio is estimated from phased heterozygous SNPs by a beta parametric model and the XCI ratio is estimated from unphased heterozygous SNPs by a semi-parametric model.

11. The process of claim 7, wherein a combination of the change in mode and magnitude of XCI and the presence or absence of at least one of the X-linked variant alleles is directly associated with a phenotype for the X-linked disorder.

12. The process of claim 11, wherein the X-linked disorder is a neurobehavioral condition manifesting at least an emotional instability, attention deficit, or delays in development and learning.

13. The process of claim 5, wherein the X-linked variant alleles comprise a chromosomal deletion, amplification, or both.

14. The process of claim 13, wherein a chromosomal deletion is detected by plotting log 2 differences, $$\log 2\left(\frac{\text{\# reads mapping to 100 bp window affected}}{\text{\# reads mapping to all windows in affected}}\right) - \log 2\left(\frac{\text{\# reads mapping to 100 bp window } mom}{\text{\# reads mapping to all windows in } mom}\right)$$

across chromosomes, where a log 2 difference of −1 means a heterozygous deletion in one of the copies, a −2 means a homozygous deletion of both copies, a +1 means a heterozygous copy gain, and a +2 means a homozygous copy gain of the chromosomal region.

15. The process of claim 14, further comprising characterizing by co-segregation analysis of parental genotypes obtained from whole exome sequencing.

16. The process of claim 1, further comprising simulating RNA sequencing reads in silico from chromosome-wide heterozygous SNP alleles of the sample and calculating an allelic skewedness ratio by analysis of phased or unphased chromosome-wide heterozygous SNP variant transcripts from the simulated data.

17. The process of claim 16, wherein the simulation of RNA sequencing reads in silico comprises:
(a) introducing nucleotide changes into a reference chromosome by selecting a number of chromosome wide SNPs from a sample;
(b) separating randomly the SNPs from the reference chromosome of interest into two groups, one group analogous to variant alleles on a maternal chromosome referred to as pseudo-maternal variant SNPs and the other group analogous to variant alleles on a paternal chromosome referred to as pseudo-paternal variant SNPs;
(c) introducing the pseudo-maternal and pseudo-paternal variant SNPs into two separate X chromosome files and reducing the two files to greater than 500 bp regions that correspond to known transcripts according to human genome annotation *Homo sapiens* to obtain two separate transcriptome files;
(d) generating paired reads mapping to the two separate transcriptome files; and
(e) sub-sampling the paired reads randomly in various ratios and merging the randomly distributed reads into a single file.

18. The process of claim 1, wherein the combined mean allelic ratio is determined with X-linked variant alleles having a minimum of 20× sequencing coverage.

19. The process of claim 1, wherein chromosome-wide allelic expression analysis provides an accurate estimate of overall expression of each X chromosome copy and serves as the basis for XCI ratio measurement.

* * * * *

SEQUENCE LISTING

```
<160> NUMBER OF SEQ ID NOS: 3

<210> SEQ ID NO 1
<211> LENGTH: 12
<212> TYPE: DNA
<213> ORGANISM: Homo sapiens

<400> SEQUENCE: 1
taattgtcag gt                                                        12

<210> SEQ ID NO 2
<211> LENGTH: 12
<212> TYPE: DNA
<213> ORGANISM: Homo sapiens

<400> SEQUENCE: 2
tatttgtcag gt                                                        12

<210> SEQ ID NO 3
<211> LENGTH: 12
<212> TYPE: DNA
<213> ORGANISM: Homo sapiens

<400> SEQUENCE: 3
taattgtcag ct                                                        12
```